US009445991B2

(12) United States Patent
Frey, II et al.

(10) Patent No.: US 9,445,991 B2
(45) Date of Patent: *Sep. 20, 2016

(54) METHODS, PHARMACEUTICAL COMPOSITIONS AND ARTICLES OF MANUFACTURE FOR ADMINISTERING THERAPEUTIC CELLS TO THE ANIMAL CENTRAL NERVOUS SYSTEM

(71) Applicants: William H. Frey, II, St. Paul, MN (US); Lusine Danielyan, Tuebingen (DE); Christoph H. Gleiter, Tuebingen (DE)

(72) Inventors: William H. Frey, II, St. Paul, MN (US); Lusine Danielyan, Tuebingen (DE); Christoph H. Gleiter, Tuebingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,210

(22) Filed: Mar. 28, 2016

(65) Prior Publication Data
US 2016/0206554 A1 Jul. 21, 2016

Related U.S. Application Data

(60) Division of application No. 13/647,066, filed on Oct. 8, 2012, which is a continuation of application No. 12/109,066, filed on Apr. 24, 2008, now Pat. No. 8,283,160.

(60) Provisional application No. 60/971,284, filed on Sep. 11, 2007.

(51) Int. Cl.
*A61K 35/30* (2015.01)
*A61K 9/00* (2006.01)
*A61K 35/28* (2015.01)

(52) U.S. Cl.
CPC ............. *A61K 9/0043* (2013.01); *A61K 35/28* (2013.01)

(58) Field of Classification Search
None
See application file for complete search history.

(56) References Cited

U.S. PATENT DOCUMENTS

| 6,180,603 | B1 | 1/2001 | Frey, II |
| 6,749,850 | B1 | 6/2004 | Finkelstein et al. |
| 7,247,310 | B1 | 7/2007 | Ohno et al. |
| 2002/0081724 | A1 | 6/2002 | Carpenter et al. |
| 2002/0169102 | A1 | 11/2002 | Frey |
| 2004/0197309 | A1 | 10/2004 | Dezawa et al. |
| 2004/0266715 | A1 | 12/2004 | Wong et al. |
| 2005/0118561 | A1 | 6/2005 | Kopyov |
| 2007/0122392 | A1 | 5/2007 | Gerecht-Nir et al. |
| 2008/0260699 | A1 | 10/2008 | Parman |
| 2009/0068155 | A1 | 3/2009 | Frey, II et al. |

FOREIGN PATENT DOCUMENTS

EP 1438942 7/2004

OTHER PUBLICATIONS

Danielyan et al. "Therapeutic Efficacy of Intranasally Delivered Mesenchymal Stem Cells in a Rat Model of Parkinson Disease" Rejuvenation Research vol. 14, No. 1, 2011, pp. 3-16.*
Li et al. "Intranasal delivery of stem cells as therapy for central nervous system disease" Experimental and Molecular Pathology, 98 (2015) 145-151.*
Danielyan et al. "Intranasal delivery of cells to the brain" European Journal of Cell Biology 88 (2009) 315-324.*
Lusine Danielyan et al: "intranasal delivery of cells to the brain", European Journal of Cell biology 88 (2009) 315-324.
Velthoven et al: "Nasal Administration of Stem cells: A Promising Novel Route to Treat Nenatal Ischemic brain Damage", Pediatric Research vol. 68, No. 2010, pp. 419-422.
Lusine Danielyan et al: "Therapeutic Efficacy of Intranasally Delivered Mesenchymal Stem Cells in a Rat Model of Parkinson Disease", Rejuvenation Research vol. 14, No. 1, 2011, pp. 3-16.
Russinoff et al: "Osteosarcoma Cells Differentiate into Phenotypes from all Three Dermal Layers" Clin Orthrop Relat Res (2911) 469-2895-2904.
Olanow et al. "Fetal nigral transplantation as a therapy for Parkinson's disease", Trends Neurosci. (1996) 19, 102-109.
Olle Lindvall, MD, PhD: "Cerebrfal Implantation in Movement Disorders: State of the Art", Movement Disorders, vol. 14, No. 2, 199, pp. 201-205.
Ni XS et al: "Autologous hematopoietic stem cell transplantation for progressive multiple sclerosis, report of efficacy and safety at three yr of follow up in 21 patients", Clin Transplant 2006: 20: 485-489 DOI. 10.1111/.1399-012-2006.0150.x.
Kopyov et al "Safety of Intratriatal Neurotransplantation for Huntington's disease Patients", Experimental Neurology 149, 97-108 (1998).
Lindvall et al: "Transplantation in Parkinson's Disease: Two Cases of Adrenal Medullary Grafts to the Putamen", Ann Neurol 22: 457-468., 1987.
Gage et al: "Grafting Genetically Modified Cells to the Brain: Possibilities for the Future", Neuroscience vol. 23, No. 3, pp. 795-807, 1987.
Breakefield et al: "Grafting genetically modified cells to the damaged brain: restorative effects of NGF expression", Science, 242, 4885 (Dec. 16, 1988): p. 1575.
Bang et al: "Autologous Mesenchymal Stem Cell Transplantatioin in Stroke Patients", Ann Neurol 2005; 57:874-882.

(Continued)

*Primary Examiner* — Thane Underdahl
(74) *Attorney, Agent, or Firm* — Barnes & Thornburg LLP

(57) ABSTRACT

Methods and compositions for preventing and treating the damaged and/or degenerating CNS experiencing loss or death of CNS cells. Various embodiments of the invention transport a therapeutically effective amount of, inter alia at least one therapeutic cell to the CNS by intranasal application to the upper-third of the nasal cavity, thereby bypassing the blood-brain barrier. A pharmaceutical composition according to the invention may comprise at least one therapeutic cell, at least one delivery-enhancement agent, at least one antibiotic, at least one regulatory factor and/or at least one immunosuppressive agent, wherein the composition is delivered to the upper-third of the nasal cavity. The therapeutic cells, once delivered to the CNS, migrate preferentially to the area of damage or degeneration or injury.

20 Claims, No Drawings

(56) References Cited

OTHER PUBLICATIONS

Nistor: "Human Embryonic Stem Cells Differentiate into Oligodendrocytes in High Purity and Myelinate After Spinal cord Transplantation", GLIA 49: 385-396 (2005).

Bjorklund et al: "Intracerebral Neural Imnats: Neuronal replacement and Reconstruction of Damaged Circuitries", Ann Rev. Neurosci. 1984 7:279:308.

Franzen et al: "Effects of Macrophage Transplantation in the Injured Adult Rate Spinal cord: A Combined Immunocytochemical and Biochemical Study", Journal of Neuroscience Research 51:316-327 (1998).

Joyce et al: "Mesenchymcal stem cells for the treatment of neurodegenerative disease", Regen Med. Nov. 2010, 5(6): 933-946, doi: 10.2217/rme.10.72.

Mason et al. "Extracellular Signals That Regulate the Tangential Migration of Olfactory Bulb Neuronal Precursors: Inducers, Inhibitors and Repellents" The Journal of Neuroscience, Oct. 1, 2001, 21(19):7654-7663.

Alexander Chausovsky et al. "Morphogenetic Effects of Neuregulin (New Differentiation Factor) in Cultured Epithelial Cells" Molecular Biology of the Cell vol. 9, 3195-3209, Nov. 1998.

Yun Liu et al. "Neuregulin-1 increase s the proliferation of neuronal progenitors from embryonic neural stem cells" Developmental Biology 283 (2005) 437-445.

Brown et al, "Intravascular Delivery of Neural Stem Cell Lines to Target Intracranial and Extracranial Tumors of Neural and Non-Neural Origin" Human Gene Therapy 14:1777-1785 (Dec. 10, 2003).

Marin et al., "Cell Migration in the Forebrain" Annu. Ref. Neurosci, 2003, 26:441-83.

Ghashghaei et al, "Neuronal migration in the adult brain: are we there yet?", 2007 Nature Publishing Group, vol. 8, Feb. 2007, pp. 141-151.

Hakanen et al., "Netrin 1 is required for neural and glial precursor migrations into the olfactory bulb" Developmental Biology 355 (2011) 101-114.

\* cited by examiner

METHODS, PHARMACEUTICAL COMPOSITIONS AND ARTICLES OF MANUFACTURE FOR ADMINISTERING THERAPEUTIC CELLS TO THE ANIMAL CENTRAL NERVOUS SYSTEM

CROSS-REFERENCE TO RELATED APPLICATIONS

This application is a divisional of patent application Ser. No. 13/647,066, filed Oct. 8, 2012, which is a continuation of application Ser. No. 12/109,066, filed Apr. 24, 2008, now U.S. Pat. No. 8,283,160 which claims the benefit of provisional patent application Ser. No. 60/971,284, filed Sep. 11, 2007, the entire contents of which are hereby incorporated herein by reference.

BACKGROUND OF THE INVENTION

1. Field of the Invention

The present invention is directed to methods and pharmaceutical compositions for administering therapeutic cells to the upper third of the nasal cavity of a mammal, thereby enabling the therapeutic cells to bypass the blood-brain barrier to prevent and/or treat the mammal's damaged and/or degenerating and/or injured central nervous system.

2. Description of the Related Art

Many neurological conditions result from damage to or the loss, i.e., death, of certain cell populations from the central nervous system through aging, disease or Injury. The cells damaged or destroyed in these conditions are not intrinsically replaced, thus the central nervous system is damaged and/or degenerating with resulting loss of function. Recent evidence demonstrates that neuronal replacement and partial reconstruction of neuronal circuitry is possible via cell transplantation therapies. Much of the initial work in the field used fetal-cell therapies. More recently, however, it has become evident that the developing and even the adult mammalian nervous system contains a population of undifferentiated, multipotent, neural stem cells that display plastic properties that are advantageous for the design of more effective neural regenerative strategies for many of these neurological conditions.

The neurological conditions, diseases and/or injuries resulting in damaged and/or degenerating CNS, i.e., cell death, comprise Alzheimer's disease, mild cognitive impairment, age-associated memory impairment, Parkinson's disease, cerebrovascular disease including stroke, Creutzfeldt-Jakob disease, familial amyotrophic lateral sclerosis, lewy-body dementia, atherosclerosis, schizophrenia, autism, tardive dyskinesia, multiple sclerosis, seizure disorders, Wilson's disease, progressive supranuclear palsy, Hallervorden-Spatz syndrome, multisystem atrophy, Huntington's disease, familial basal ganglia degeneration, Down's syndrome, cataracts, haemochromatosis, thalassemia, cerebral hemorrhage, subarachnoic hemorrhage, head injury, and spinal cord injury. Moreover, certain medical procedures, for example coronary artery bypass graft (CABG) surgery, are associated with neurological complications that result in damage and/or degeneration of the central nervous system and concomitant cell death. In the case of CABG, the surgery is performed on more than 800,000 patients worldwide each year. Many of the CABG procedures performed are associated with neurological complications. These complications range from stroke in up to 16% of the patients to general cognitive decline with 50% of patients having impairment post-surgery and with progressive decline occurring in some patients over the next five years. In addition, physical and behavioral impairment manifest in some CABG patients. Newman M F et al., N. Eng. J. Med. 344:395-402 (2001); Brillman J., Neurol. Clin. 11:475-495 (1993); and Seines, O. A., Ann. Thorac. Surg. 67:1669-1676 (1999) are instructive.

Neural stem cells have been demonstrated to replace lost and dying cells and lost neural circuits in the damaged and/or degenerating CNS in cell replacement therapies. For instance, treatment of mice with MPTP, a drug that selectively destroys dopaminergic cells in the brain stem, followed by grafting with a neural stem cell population, resulted in a reconstituted dopaminergic cell population composed of both donor and host cells. Similar studies in mice using a hypoxia-ischemic brain injury model showed transplantation of neural stem cells enhanced the recovery of the damaged system (Park et al. (1999) J. Neurotrauma 16:675-687 and Park et al. (1997) Soc. Neurosci. Abst. 23:346). In patients with stroke, the transplantation of cells from a human neuronal cell line showed improvement of neurological function. (Kondziolka D., et al., (2000) "Transplantation of cultured human neuronal cells for patients with stroke". Neurology. 55:565-9). In a mouse model of Alzheimer's disease, the transplantation of neural stem cells into the prefrontal and parietal cortices dramatically alleviated the cholinergic deficits and recent memory disruption associated with AD. (Wang, Q., et al., (2006) "Neural stem cells transplantation in cortex in a mouse model of Alzheimer's disease. J Med Invest., 53:61-9).

Further, in Parkinson's disease, the neurons that degenerate in the mammalian central nervous system comprise the dopaminergic neurons of the substantia nigra. Current cell replacement strategies for patients with advanced Parkinson's disease comprise intrastriatal grafts of nigral dopaminergic neurons from 6- to 9-week-old human embryos. Clinical improvements develop gradually over the first 6-24 months after transplantation (Olanow et al. (1996) Trends Neurosci. 19:102-109 and Lindvall et al. (1999) Mov. Disord. 14:201-205). It has been shown that stem cell transplants of different origin, e.g., hematopoietic, embryonic, result in several clinical benefits in patients with severe Parkinson's disease. (Freed, C R, et al. (Transplantation of embryonic dopamine neurons for severe Parkinson's disease. N Engl J Med 2001; 344:710-719).

Similar benefits were realized with progressive multiple sclerosis patients. (Ni X S, et al., (2006) "Autologous hematopoietic stem cell transplantation for progressive multiple sclerosis: report of efficacy and safety at three yr of follow up in 21 patients" Clin Transplant. 20:485-9) (further suggesting that MS treatment should combine immunomodulation with neuroprotective modulaties such as cell-based therapy to achieve maximal clinical benefit).

Further, the first study of human fetus-to-adult striatal transplantation has been performed in three nondemented patients with moderately advanced Huntington disease. Magnetic resonance imaging evaluation at 1 year documented graft survival and growth without displacement of surrounding tissue. All patients improved on some measure of cognitive function. (Kopyov et al. (1998) J. Exp. Neurol. 149:97-108). See also, Date et al. (1997) J. Exp. Neurol. 147:10-17.

Each of the known models and methods for therapeutic cell-based therapies require surgical intervention, i.e., transplantation, of neural stem cells using invasive grafting techniques and/or systemic delivery methods that do not target the damaged areas of the central nervous system. It would be highly advantageous to provide a method, pharmaceutical composition and/or article of manufacture or kit that would provide therapeutic cells, including but not limited to neural stem cells, in a non-invasive and highly targeted manner.

For example, it would be advantageous to deliver such therapeutic cells to the degenerating central nervous system in such a way as to avoid systemic exposure. No known method or pharmaceutical composition currently provides such advantages. The present invention provides these advantages by applying the therapeutic cells to the upper third of the nasal cavity, thereby bypassing the blood-brain barrier and administering the therapeutic cells and other compounds directly to the central nervous system.

Certain embodiments of the present invention comprise nasal and/or mucosal antibiotics to assist in protecting the subject patient from nasal bacteria migrating along the neural pathway followed by the applied therapeutic cells and/or pharmaceutical compound. Such antibiotics are well known as applied topically, but none are administered as a pretreatment, co-treatment and/or post-treatment, either systemically and/or intranasally, in conjunction with intranasal application of therapeutic cells and/or pharmaceutical compound.

For example, in one study, mupirocin smeared inside the nose cut infection rates in half or better Staphylococcus aureus is a widely distributed germ that normally resides in the nostrils of an estimated 25 to 30 percent of all hospitalized patients without causing harm. But this bacteria can contaminate surgical sites, causing severe and often deadly infections, especially in people with weakened immune systems.

Another study found that nasal xylitol, an over the counter remedy sold in health food stores, can reduce nasal bacteria and their ability to hold onto and infect cells in the nasal mucosa. Still other studies have found that defensins, a natural antibiotic found in mucosa in the human, can protect against bacterial infection and enhance immune protective function. Mammalian defensins are small, cationic, antimicrobial peptides encoded by the host that are considered to be important antibiotic-like effectors of innate immunity. By using chemokine receptors on dendritic cells and T cells, defensins might also contribute to the regulation of host adaptive immunity against microbial invasion. Defensins have considerable immunological adjuvant activity and linkage of beta-defensins or selected chemokines to an idiotypic lymphoma antigen has yielded potent antitumor vaccines. The functional overlap between defensins and chemokines is reinforced by reports that some chemokines have antimicrobial activities. Although showing similarity in activity and overall tertiary structure, the evolutionary relationship between defensins and chemokines remains to be determined. (De Yang, et al., Mammalian defensins in immunity: more than just microbicidal. Trends Immunol. 2002 June; 23 (6):291-6 12072367).

Moreover, it is well known that regulatory agents comprising trophic and growth factors such as erythropoietin (EPO), brain-derived neurotrophic factor (BDNF), nerve growth factor (NGF), fibroblast growth factor (FGF) and epidermal growth factor (EGF) play a crucial role in in-vitro and in-vivo survival and differentiation of stem cells (Erickson et al., Roles of insulin and transferrin in neural progenitor survival and proliferation. J Neurosci Res. 2008 Feb. 21; Bossolasco et al., Neuro-glial differentiation of human bone marrow stem cells in vitro. Exp Neural, 2005 June; 193(2):312-25). The better survival of surgically transplanted cells was shown in the case of simultaneous application of EPO (Kanaan et al., Exogenous erythropoietin provides neuroprotection of grafted dopamine neurons in a rodent model of Parkinson's disease. Brain Res. 2006 Jan. 12; 1068(1):221-9). However, it is not known to introduce such regulatory factors or agents in conjunction with the intranasal application of therapeutic cells and/or pharmaceutical compositions thereof, to the upper third of the nasal cavity, thus bypassing the blood-brain barrier.

In addition, it is well known that regulatory agents comprising various growth factors including insulin-like growth factor-I (IGF-I), nerve growth factor (NGF), and basic fibroblast growth factor (bFGF), regulate the survival and differentiation of nerve cells during the development of the peripheral and central nervous systems. Regulatory agents such as neurotrophins are also required for nerve growth during development (Tucker et al. (2001) Nature Neurosci, 4:29-37). In the mature nervous system, these trophic factors maintain the morphologic and neurochemical characteristics of nerve cells and strengthen functionally active synaptic connections. Such regulatory factors find use in enhancing the methods of cell-replacement therapies according to the present invention.

For instance, bFGF enhances survival and growth of neurons in vitro. Further, bFGF produces a potent growth promoting effect on implanted neurons in vivo when the implanted neurons are genetically engineered to express the bFGF (Takayama et al. (1995) Nat. Med. 1:53-8). In addition, implantation of polymer-based bioactive rods that secrete epidermal growth factor and bFGF into transplanted fetal ventral mesencyphalic tissue result in both improved functional characteristics and enhanced cell survival (Tornquvist et al. (2000) Exp. Neurol. 164:130-138).

Nerve growth factor (NGF) has also been shown to influence grafted tissue in the CNS. For example, ChAT activity, an assay indicative of cholinergic cell activity, was elevated significantly in cholinergic neurons that were transplanted into brain tissue that contained an NGF-releasing pellet adjacent to the grafted cells (Mahoney et al. (1999) Med. Sci. 96:4536-4539). IGF-I has also been shown to promote differentiation of post-mitotic mammalian CNS neuronal stem cells and to influence apoptosis of human erythroid progenitor cells. See, for example, Arsenijevic et al. (1998) J. Neurosci. 18:2118-2128; Tanigachi et al. (1997) Blood 90:2244-2252; Reboarcet et al. (1996) J. Biol. Reprod. 55:1119-1125; Muta et al. (1994) J. Clin. Invest. 94:34-43; and, Muta et al. (1993) J. Cell. Phys. 156:264-271. Additionally, it has been shown that certain growth associated proteins, such as, GAP-43 and CAP-23 act to promote regeneration of injured axons and may support regeneration in the spinal cord and CNS. See, for example, Bomze et al. (2001) Nature Neurosci. 4:38-43 and Woolf et al. (2001) Nature Neurosci. 4:7-9.

Administration of regulatory agents as a means of improving the clinical outcome of a mammal having undergone a neural regenerative, i.e., therapeutic cell-based strategy has, however, been meet with difficulty. Generally, these agents cannot be administered systemically. Furthermore, many of these regulatory agents do not cross the blood-brain barrier efficiently. Intracerebroventricular administration, while possibly an effective method for delivering regulatory agents, is an invasive technique that is not preferred in a clinical setting. Implantation of polymers containing regulatory agents is also invasive and is further limited by the relatively small radius surrounding the polymer implant in which the regulatory agent is capable of eliciting an effect. Additionally, while genetic engineering of the transplanted cells to express regulatory agents has been performed, stable transfection and survival of the cells following implantation continues to be problematic.

The present invention provides solutions for, inter alia, these problems.

SUMMARY OF THE INVENTION

Given the situation described above there is a need for a method for efficient and non-invasive delivery of therapeutic cells and/or pharmaceutical compositions to the damaged and/or degenerating central nervous system.

The present invention is directed to, inter alia, the prevention and/or treatment of the damaged and/or degenerating central nervous system due to a disease or other condition that causes the loss or death of CNS cells. Specifically, the present invention provides a method, pharmaceutical composition and article of manufacture for transporting a therapeutically effective amount of at least one therapeutic cell to the CNS by intranasal application to the upper third of the nasal cavity, thereby bypassing the blood-brain barrier and avoiding unwanted systemic exposure as well as invasive delivery methods.

Various embodiments of the present invention comprise intranasal prevention, pretreatment, post-treatment and/or as a component of the pharmaceutical composition comprising therapeutic cells of a therapeutically effective amount of a delivery-enhancement agent(s) to enhance delivery of the therapeutic cell(s) to the CNS. Still other embodiments comprise at least one antibiotic applied intranasally and/or systemically as a pretreatment, a co-treatment (either administered simultaneously or as a component of the therapeutic composition comprising therapeutic cells) and/or a post-treatment device to protect the patient during therapeutic cell therapy. Still other embodiments comprise administering a therapeutically effective amount of at least one regulatory agent to the upper third of the mammalian nasal cavity as a pretreatment, post-treatment and/or as part of the pharmaceutical composition comprising the therapeutic cells. Still other embodiments comprise at least one immunosuppressive agent applied intranasally and/or systemically as a pretreatment, a co-treatment (either administered simultaneously or as a component of the therapeutic composition comprising therapeutic cells) and/or a post-treatment device to enhance the viability of therapeutic cells in vivo during therapeutic cell therapy. The present invention finds use in improving the clinical outcome of a mammal having undergone a neural regenerative strategy comprising the bypassing of the blood-brain barrier of therapeutic cells transported directly into the CNS of the mammal.

Various embodiments of the invention relate to methods and pharmaceutical compositions for preventing and treating neurological damage and degeneration, i.e., cell loss and death within the CNS and the resulting effects, including but not limited to treating memory loss and improving memory loss, due to cerebral ischemia and/or neurodegeneration for patients at risk for, or diagnosed with, certain medical conditions such as Alzheimer's disease, mild cognitive impairment, age-associated memory impairment, Parkinson's disease, cerebrovascular disease including stroke, Creutzfeldt-Jakob disease, familial amyotrophic lateral sclerosis, lewy-body dementia, atherosclerosis, schizophrenia, autism, tardive dyskinesia, multiple sclerosis, seizure disorders, Wilson's disease, progressive supranuclear palsy, Hallervorden-Spatz syndrome, multisystem atrophy, Huntington's disease, familial basal ganglia degeneration, Down's syndrome, cataracts, haemochromatosis, thalassemia, cerebral hemorrhage, subarachnoid hemorrhage, head injury, spinal cord injury and metabolic disorders affecting the CNS.

DETAILED DESCRIPTION OF THE INVENTION

Definitions

As used herein, "central nervous system" (CNS) refers to the brain and spinal cord and associated tissues.

As used herein, "neurological disorders and diseases of the CNS" refers to brain diseases and conditions that comprise ischemia, i.e., cerebral ischemia, ischemia, stroke, neurodegeneration, neurological complications arising from such as Alzheimer's disease, Parkinson's disease, Wilson's disease, Lewy body dementia, multiple sclerosis, seizure disorders, cerebellar ataxia, progressive supranuclear palsy, amyotrophic lateral sclerosis, autism, affective disorders, anxiety disorders, metabolic disorders that affect the CNS, and/or schizophrenia; cell damage; nerve damage from cerebrovascular disorders such as stroke in the brain or spinal cord, from CNS infections including meningitis and HIV, from tumors of the brain and spinal cord, prion diseases, and CNS disorders resulting from ordinary aging (e.g., anosmia), head and/or brain injury, or spinal cord injury and any other medical diseases and conditions mentioned herein with neurological cell loss, damage and/or degeneration.

An "effective amount" of cells and/or agent is an amount sufficient to prevent, treat, reduce and/or ameliorate the symptoms and/or underlying causes of any of the above disorders or diseases. In some instances, an "effective amount" is sufficient to eliminate the symptoms of those diseases and, perhaps, overcome the disease itself. Preferably, an effective amount of the subject cell in the dose range of $50$-$10^8$ cells for chronic or single application and/or an effective amount of agent in the dose range of 0.001-2.0 mg/kg yields a tissue concentration of $10$-$10^5$ cells per ml tissue and of agent in the range of about $10^{-13}$ molar to about $10^{-5}$ molar, but the concentrations may be greater provided that toxicity is avoided.

In the context of the present invention, the terms "treat" and "therapy" and the like refer to alleviate, slow the progression, prophylaxis, attenuation or cure of existing disease or condition that has or is causing cell death in the CNS. "Prevent", as used herein, refers to putting off, delaying, slowing, inhibiting, or otherwise stopping, reducing or ameliorating the onset of such diseases or disorders. It is preferred that a large enough quantity of the cell(s) and/or agent(s) be applied in non-toxic levels in order to provide an effective level of activity against the disease. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

"Therapeutic cells(s)" is defined herein to comprise at least one cell or type of cell, for example and without limitation a neural stem cell, that is transported via intranasal application to the upper third of the subject's nasal cavity and into the damaged and/or degenerating CNS of the subject undergoing cell-replacement therapy. The therapeutic cell(s) may be derived from any source and may be at various stages of developmental differentiation as long as the therapeutic cell(s) are sufficient to prevent or reduce the morphological and/or behavioral neurological symptoms of the neurological disorder, disease and/or condition being treated with cell-replacement therapy according to the present invention. Moreover, it is recognized that the therapeutic cell(s) may be either heterologous or autologous to the host. By heterologous it is intended that the therapeutic cell is derived from a mammal other than the patient subject, while an autologous therapeutic cell is derived from the patient subject, manipulated ex vivo, and transported back into the patient subject's CNS by methods of the present invention. Therapeutic lymphocytes may also administered to the upper third of the nasal cavity using the present invention to target both the central nervous system and lymphatics. Lymphocytes function as part of the body's defenses and include natural killer cells (NK cells), T cells and B cells. Such cells can be useful in the treatment of brain tumors and other CNS and lymphatic disorders. Further discussion of therapeutic cells is undertaken infra, each such aspect is included in the definition of "therapeutic cells".

As used herein, "regulatory agent" refers to any molecule having a growth, proliferative, differentiative, or trophic effect on a transplanted donor cell of the present invention. Any regulatory agent that is capable of regulating the development of the transplanted donor cell can be administered by the methods of the present invention. See, for example, Mackay-Sim et al. (2000) Prog. Neurobiol. 62:527-559, herein incorporated by reference. Further discussion of regulatory agent(s) is undertaken infra, each such aspect is included in the definition of "regulatory agent".

In the context of the present invention, the terms "treat" and "therapy" and "therapeutic" and the like refer to alleviate, slow the progression, prophylaxis, attenuation or cure of a damaged or degenerating CNS involving loss or death of CNS cells. The definition further comprises putting off, delaying, slowing, inhibiting, or otherwise stopping, reducing or ameliorating the damage or degenerating CNS involving loss or death of CNS cells. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

As used herein, the terms "differentiate" and "mature" refer to the progression of a cell from a stage of having the potential to differentiate into at least two different cellular lineages to becoming a specialized cell. Such terms can be used interchangeably for the purposes of the present invention. The term "lineage" refers to all of the stages of the developmental cell type, from the earliest precursor cell to a completely mature cell (i.e., a specialized cell). Accordingly, the transported therapeutic cells of the present invention can be derived from a multipotent cell lineage, preferably a neural lineage, and may be in any stage of differentiation. Thus, the present invention includes therapeutic cells that are naturally programmed to differentiate into only one type of lineage. These types of cells can include some kinds of fibroblasts or simply differentiated astroglia, neurons, oligodendrocytes, microglia or endothelial cells, and they may be derived or just isolated from the tissue of a dead donor.

Further aspects of these terms are discussed infra, each such aspect is included within the definition of the terms.

As used herein, the term "multipotent stem cell" refers to a cell capable of differentiating into a variety of lineages. Multipotent therapeutic, e.g., stem, cells are characterized by their ability to undergo continuous cellular proliferation, to regenerate exact copies of themselves (self-renewal), to generate a large number of regional cellular progeny, and to elaborate new cells in response to injury or disease. A "multipotent population of cells" refers to a composition of cells capable of differentiating into less than all lineages of cells but at least into two cell lineages. Current studies have demonstrated that multipotent stem cells from a non-neurologic region are not lineage-restricted to their developmental origin, but can generate region-specific neurons when exposed to the appropriate environmental cues (Lamga et al. (2001) J. Neurosci. 20:8727-8735).

A "neural stem cell" is defined herein as a multipotent cell that is an immature and uncommitted multipotent cell that exists in the nervous system (Ourednik et al. (1999) Clinical Genetics 56:267-278). Under specific conditions, the neural stem cell is capable of producing daughter cells that can terminally differentiate into neurons and glia (i.e., astrocytes (type I and II) and oligodendrocytes). They exist in both the developing nervous system and in the adult nervous system. A detailed characterization of the properties of neural stem cells can be found in, for example, McInnes et al. (1999) Clin. Genet. 56:267-278.

A "neuronal progenitor cell" is an undifferentiated cell that is derived from a neural stem cell and which has committed to a particular path of differentiation, does not exhibit self-maintenance, and under appropriate conditions will differentiate into neuroblasts (neuron generating cells) or fibroblasts (glia generating cells). The use of such multipotent neuronal cell lineages for transplantation is known in the art. See, for example, Snyder et al.(1992) Cell 68:33, where multipotent neuronal cell lines have been grafted into the rat cerebellum to form neurons and glial cells. See also, Campell et al. (1995) Neuron 15:1259-1273; Fishell et al. (1995) Development 121:803-812; and, Olsson et al. (1995) Eur. J. Neurosci. 10:71-85.

"Ischemia" or ischemic episode or condition is defined herein to comprise an ischemic condition where the brain or parts of the brain do not receive enough blood flow to maintain normal neurological function, resulting in a loss or death of CNS cells and concomitant damage and/or degeneration of the CNS. Various conditions and/or diseases can cause ischemia, including but not limited to stroke. Some of the neurological disorders and diseases of the CNS defined and discussed herein are characterized by some level of ischemia. The neurological disorders and diseases of the CNS defined and discussed herein are amenable to treatment with the therapeutic cell replacement strategies of the present invention.

An "effective amount" of therapeutic cells and/or component(s) of the pharmaceutical composition of the present invention comprising therapeutic cells is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and overcome the disease itself. For illustrative purposes only, exemplary treatment regimens relating generally to the therapeutic agents disclosed herein, including dosage ranges, volumes and frequency are provided below:

Efficacious dosage range for delivery-enhancement agents, regulatory agents, immunosuppressive agents and/or antibiotics comprises 0.0001-1.0 mg/kg.

A more preferred dosage range may be 0.005-1.0 mg/kg.

The most preferred dosage range may be 0.05-1.0 mg/kg.

The "effective amount" of therapeutic cells, i.e., efficacious dosage range, comprises 50 cells-$10^8$ cells A more preferred dosage range for therapeutic cells comprises $10^3$ cells-$10^8$ cells.

The most preferred dosage range for therapeutic cells comprise $10^4$ cells-$10^8$ cells.

The dosage volume (applicable to nasal sprays or drops) range may be 0.015 ml-1.0 ml.

The preferred dosage volume (applicable to nasal sprays or drops) range may be 0.03 ml-0.6 ml.

The brain concentrations that are likely to be achieved with the dosage ranges provided above are, for a single dose: 10-$10^8$ cells per ml tissue and 0.1 nM-5 µM.

Over the course of a multi-dose treatment plan, the maximum brain concentration may be as high as $10^6$ cells per ml tissue and 50 µM for deliver-enhancement agents, regulatory agents, immunosuppressive agents and antibiotics.

The present invention therefore provides methods and pharmaceutical compositions to improve cell-based therapies used to regenerate neural tissue that has been damaged or is undergoing degeneration by any CNS disease or disorder, i.e., loss or death of CNS cells. CNS disorders that are within the scope of the present invention comprise, for example, head injury, spinal cord injury, stroke, and ischemia. CNS disorders within the scope of the present invention also comprise neurodegenerative diseases such as, but not limited to, brain diseases and conditions that comprise ischemia, i.e., cerebral ischemia, ischemia, stroke, neurodegeneration, neurological complications arising from such as Alzheimer's disease, Parkinson's disease, Wilson's disease, Lewy body dementia, multiple sclerosis, cerebellar ataxia, progressive supranuclear palsy, amyotrophic lateral sclerosis, affective disorders, anxiety disorders, autism and/or schizophrenia; cell damage; nerve damage from cerebrovascular disorders such as stroke in the brain or spinal cord, from CNS infections including meningitis and HIV, from tumors of the brain and spinal cord, prion diseases, and CNS disorders resulting from ordinary aging (e.g., anosmia), brain injury, spinal cord injury and/or metabolic disorders affecting the CNS.

Accordingly, the embodiments of the present invention find utility in enhancing the regeneration or repair of damaged neuronal tissue in an animal having undergone a neural regenerative, i.e., cell-based, strategy that comprises the intranasal application via the upper third of the subject animal nasal cavity, thereby bypassing the blood-brain barrier, of at least one therapeutic cell into the CNS of the mammal to treat a neurological disease or disorder of the CNS involving ischemia and/or CNS cell loss or death.

Neural regenerative strategies comprising the transplantation of donor cells into the CNS of a host are known in the art. However, it is not known to bypass the blood-brain barrier with therapeutic cells, thus transporting such cells directly into the damaged or degenerating CNS of a host subject by intranasal application to the upper third of the nasal cavity. The therapeutic cell may be aided in transportation by at least one delivery-enhancement agent, in viability by at least one immunosuppressive agent, and/or developmentally regulated by at least one regulatory agent, while the patient may be protected from mucosal bacteria bypassing the blood-brain barrier through use of at least one antibiotic, each of which may administered by the method of the present invention and, as will be further discussed below, some of the components of the therapeutic method may be administered systemically and/or intranasally.

Transportation Pathway to Bypass Blood-Brain Barrier
The Olfactory Nerve

Various methods of the present invention include administration of the therapeutic cells and/or pharmaceutical composition(s) of the present invention to tissue innervated by the olfactory nerve and that is located in the upper third of the nasal cavity. The therapeutic cells and/or pharmaceutical composition(s) of the present invention can be delivered to the olfactory area via application to the upper third of the nasal cavity.

Fibers of the olfactory nerve are unmyelinated axons of olfactory receptor cells that are located in the upper one-third of the nasal mucosa. The olfactory receptor cells are bipolar neurons with swellings covered by hair-like cilia that project into the nasal cavity. At the other end, axons from these cells collect into aggregates and enter the cranial cavity at the roof of the nose. Surrounded by a thin tube of pia, the olfactory nerves cross the subarachnoid space containing CSF and enter the inferior aspects of the olfactory bulbs. Once the therapeutic cells and/or pharmaceutical composition(s) of the present invention is applied to the upper third of nasal cavity, the therapeutic cells and/or pharmaceutical composition(s) of the present invention can undergo transport through the nasal mucosa and into the olfactory bulb and other areas of the CNS, such as the anterior olfactory nucleus, frontal cortex, hippocampal formation, amygdaloid nuclei, nucleus basalis of Meynert, hypothalamus, midbrain, cerebellum, cervical spinal cord and the like.

Neuronal Transport

Embodiments of the present method includes administration of the therapeutic cells and/or pharmaceutical composition(s) of the present invention to the subject by application to the upper third of the mammalian subject's nasal cavity. Application of the therapeutic cells and/or pharmaceutical composition(s) of the present invention in this manner ensures that the therapeutic cells and/or pharmaceutical composition(s) are transported to the CNS, brain, and/or spinal cord along a neural pathway, with reduced systemic loss and systemic exposure. A neural pathway includes transport within or along a neuron, through or by way of lymphatics running with a neuron, through or by way of a perivascular space of a blood vessel running with a neuron or neural pathway, through or by way of an adventitia of a blood vessel running with a neuron or neural pathway, or through an hemangiolymphatic system.

The present invention comprises transportation of the therapeutic cells and/or pharmaceutical composition(s) by way of a neural pathway, rather than through the circulatory system, so that regulatory agents that are unable to, or only poorly, cross the blood-brain barrier from the bloodstream into the brain can be delivered to the lymphatic system, CNS, brain, and/or spinal cord. The therapeutic cells and/or pharmaceutical composition(s) of the present invention, once past the blood-brain barrier and in the CNS, can then be delivered to various areas of the brain or spinal cord through lymphatic channels, through a perivascular space, or transport through or along neurons. In one embodiment, the therapeutic cells migrate to the region of damage and/or degeneration within the CNS.

Use of a neural pathway to transport a regulatory agent to the brain, spinal cord, or other components of the central nervous system obviates the obstacle presented by the blood-brain barrier so that medications, i.e., therapeutic cells and/or pharmaceutical compositions of the present invention, that cannot normally cross that barrier, can be delivered directly to the CNS, e.g., the brain and spinal cord. In addition, the present invention can provide for delivery of a more concentrated level of the therapeutic cells and/or pharmaceutical composition(s) of the present invention to neural cells since the therapeutic cells and/or pharmaceutical composition(s) of the present invention do not become diluted in fluids present in the bloodstream. As such, the invention provides an improved method for delivering the therapeutic cells and/or pharmaceutical composition(s) of the present invention to the CNS including the brain and/or spinal cord.

The Olfactory Neural Pathway

One embodiment of the present method includes delivery of the regulatory agent to the subject in a manner such that the regulatory agent is transported into the CNS, e.g., the brain, and/or spinal cord along an olfactory neural pathway. Typically, such an embodiment includes administering the regulatory agent to tissue innervated by the olfactory nerve and inside the nasal cavity. The olfactory neural pathway innervates primarily the olfactory epithelium in the upper third of the nasal cavity, as described above. Application of the regulatory agent to a tissue innervated by the olfactory nerve can deliver the regulatory agent to damaged neurons or cells of the CNS, brain, and/or spinal cord. Olfactory neurons innervate this tissue and can provide a direct connection to the CNS, brain, and/or spinal cord due, it is believed, to their role in olfaction.

Delivery through the olfactory neural pathway can employ lymphatics that travel with the olfactory nerve to the various brain areas and from there into dural lymphatics associated with portions of the CNS, such as the spinal cord. Transport along the olfactory nerve can also deliver regulatory agents to an olfactory bulb. A perivascular pathway and/or a hemangiolymphatic pathway, such as lymphatic channels running within the adventitia of cerebral blood vessels, can provide an additional mechanism for transport of therapeutic regulatory agents to the brain and spinal cord from tissue innervated by the olfactory nerve.

Therapeutic cells and/or pharmaceutical compositions thereof may be administered to the olfactory nerve, for example, through the olfactory epithelium located at the upper third of the nasal cavity. Such administration can employ extracellular or intracellular (e.g., transneuronal) anterograde and retrograde transport of the regulatory agent entering through the olfactory nerves to the brain and its meninges, to the brain stem, or to the spinal cord. Once the therapeutic cells and/or pharmaceutical composition thereof is dispensed into or onto tissue innervated by the olfactory nerve, the therapeutic cells and/or pharmaceutical composition and/or components thereof may be transported through the tissue and travel along olfactory neurons into areas of the CNS including the brain stem, cerebellum, spinal cord, cerebrospinal fluid, olfactory bulb, and cortical and subcortical structures.

The blood-brain barrier is bypassed in the present invention by application of the therapeutic cells and/or pharmaceutical composition(s) comprising therapeutic cells by application to the upper third of the nasal cavity. The therapeutic cells and/or pharmaceutical composition of the invention migrate from the nasal mucosa through foramina in the cribriform plate along the olfactory neural pathway and into the CNS. See Example 1 infra providing experimental evidence that the blood-brain barrier is bypassed in the hypothesized manner.

Administration to the nasal cavity employing a neural pathway can thus deliver therapeutic cells, including but not limited to eukaryotic cells and stem cells, and/or pharmaceutical composition comprising therapeutic cells of the present invention to the lymphatic system, brain stem, cerebellum, spinal cord, and cortical and subcortical structures. The therapeutic cells and/or pharmaceutical composition of the present invention alone may facilitate this movement into the CNS, i.e., brain, and/or spinal cord. Alternatively, a carrier and/or the delivery-enhancement agent(s) may assist in the transport of the therapeutic cells and/or pharmaceutical composition of the present invention into and along the neural pathway. Administration of a therapeutic cells and/or pharmaceutical composition of the present invention to the upper third of the nasal cavity thus bypasses the blood-brain barrier through a transport system from the nasal mucosa and/or epithelium to the CNS, i.e., brain and spinal cord.

Various embodiments of the invention administer the therapeutic cells and/or pharmaceutical composition(s) of the present invention to tissue innervated by the olfactory nerves. Such nerve systems can provide a direct connection between the outside environment and the brain, thus providing advantageous delivery of a regulatory agent to the CNS, including brain, brain stem, and/or spinal cord. The therapeutic cells and/or pharmaceutical composition(s) of the present invention are unable to cross or inefficiently cross the blood-brain barrier from the bloodstream into the brain. Thus, the methods of the present invention allow for the delivery of the inventive therapeutic cells and/or pharmaceutical composition(s) by way of the olfactory nerve rather than through the circulatory system. This method of administration allows for the efficient delivery of the therapeutic cells and/or pharmaceutical composition(s) of the present invention to the CNS, brain, or spinal cord without systemic loss or exposure.

The immunosuppressive agent(s) and/or antibiotic(s) may be delivered according to various embodiments of the present invention either systemically or to the upper third of the nasal cavity either alone, or in the pharmaceutical combination comprising therapeutic cell(s).

Alternative Pathways

Alternative pathways to the olfactory nerve pathway discussed above comprise pathways along other nerves that innervate the nasal cavity, e.g., the trigeminal pathway, well known to the skilled artisan.

Therapeutic Cells

The therapeutic cell(s) of the present invention can be derived from any fetal or adult mammalian tissues, including bone marrow, or neural tissues, including tissue from the hippocampus, olfactory epithelium, olfactory bulb, subventricular zone, cerebellum, spinal cord, cortex (i.e., motor or somatosensory cortex), striatum, basal forebrain (cholenergic neurons), ventral mesencephalon (cells of the substantia nigra), and the locus ceruleus (neuroadrenaline cells of the central nervous system). Moreover, the therapeutic cell(s) may include, but are not limited to, neural and/or multipotent stem cells, neural progenitor cells, genetically engineered cells, t-cells and/or autologous cells.

The developing and the adult animal central nervous system contains a population of neural stem cells and progenitor cells that are of particular interest in the present invention as therapeutic cells. Methods of isolation and transplantation of various neural progenitor cells derived from different tissues at different developmental stages are known in the art and include, for example, striatum cortex (Winkler et al. (1998) Mol. Cell. Neurosci. 11:99-116; Hammang et al. (1997) Exp. Neural. 147:84-95); cortex (Brustle et al. (1998) Nat. Biotechnol 16:1040-1044 and Sabate et al. (1995) Nat. Genet 9:256-260); human telencephalon (Flax et al (1998) Nature 392:18-24 and Vescovi et al, (1999) Neuron 11:951-966); hippocampus (Gage et al. (1995) J. Neurobiol. 36:249-266 and Suhonen et al. (1996) Nature 383:624-627); basal forebrain (Minger et al. (1996) Exp. Neurol. 141:12-24); ventral mesencephalon (Winkler et al. (1998) Mol. Cell. Neurosci. 11:99-116; Svendsen et al. (1996) Exp. Neural 137:376-388; Hammang et al. (1997)

Exp. Neurol. 147:84-95; Studer et al. (1997) Nat. Neurosci. 1:290-295; Milward et al. (1997) J. Neurosci. Res. 50:862-871); and subventricular zone (Milward et al. (1997) Milward et al. (1997) J. Neurosci. Res. 50:862-871). Each of these references is herein incorporated by reference. In addition, methods for the isolation of neural stem cell progeny and method to promote their differentiation can also be found in U.S. Pat. No. 6,071,889 and U.S. Pat. No. 6,103,530, both of which are herein incorporated by reference.

Therapeutic cells of the present invention may also be of paraneural origin. A preferred example of such a cell is the adrenal medullar chromafin cell. See, for example, Bjorklund et al. (1985) Neural Grafting in the Mammalian CNS (Amsterdam: Elsevier), pp. 3-11, and Lindvall et at (1997) Ann. Neurol 22: 457-468, which demonstrate the usefulness of chromafin cells for the treatment of Parkinson's disease.

Therapeutic cells of the present invention that are not of neural origin, but which have been altered to produce a substance of neurological interest, are also within the inventive scope. A preferred cell type is a human foreskin fibroblast, which is easily obtained and cultured (see, for example, U.S. Pat. No. 6,060,048). Such cells are preferably genetically altered, using methods known in the art, to express neuronal growth factors, neurotransmitters, neuropeptides, or enzymes involved in brain metabolism. See, for example, Gage et al. (1987) Neurosci. 23: 795-807; Rosenberg et al. (1988) Science 242: 1575-1578; Shimohama et al. (1989) Mol. Brain Res. 5: 271-278; which are hereby incorporated by reference. Alternatively, therapeutic cells derived from a non-neuronal origin, such as epidermal cells, may be converted or transdifferentiated into different types of neuronal cells. See, for example, U.S. Pat. No. 6,087,168.

The therapeutic cell(s) of the present invention may be genetically altered prior to transplantation into the host. As used herein, the term "genetically altered" refers to a cell into which a foreign nucleic acid, e.g., DNA, has been introduced. The foreign nucleic acid may be introduced by a variety of techniques, including, but not limited to, calcium-phosphate-mediated transfection, DEAE-mediated transfection, microinjection, viral transformation, protoplast fusion, and lipofection. The genetically altered cell may express the foreign nucleic acid in either a transient or long-term manner. In general, transient expression occurs when foreign DNA does not stably integrate into the chromosomal DNA of the transfected cell. In contrast, long-term expression of foreign DNA occurs when the foreign DNA has been stably integrated into the chromosomal DNA of the transfected cell.

Such genes of interest include neurotransmitter-synthesizing enzymes (i.e., tyrosine hydrolase (TH) and cholineacetyltransferase). Such methods are commonly known in the art. For instance, therapeutic donor cells from various regions of the brain and at different stages of development have been isolated and have been immortalized via genetic alteration. For example, olfactory and cerebellum cells have been immortalized using the viral myc (v-myc) oncogene to generate cell lines with neuronal and glial phenotypes (Ryder et al. (1990) J. Neurobiol. 21:356). Similar studies by Snyder et al. ((1992) Cell 68:33) resulted in multipotent neuronal cell lines that were engrafted into the rat cerebellum to form neurons and glial cells. In other studies, murine neuroepithelial cells were immortalized with a retrovirus vector containing c-myc and were cultured with growth factors to form differentiated cell types similar to astrocytes and neurons (Barlett et al. (1988) Proc. Natl. Acad. Sci. USA 85:3255).

Moreover, intranasally delivered therapeutic genetically-engineered cells of the present invention may comprise biological factories that can enter the CNS and release substances that are deficient or are missing in the patients' CNS. For example, in lipid storage diseases and hereditary metabolic disorders such as phenylketoneuria (PKU), Wilson's disease, Tay Sachs, lysosomal storage diseases, or Nieman Pick disease, there may be an enzyme missing in the brain from birth. Therapeutic cells of the present invention may comprise that specific missing enzyme. Such genetically-engineered therapeutic cells may then be delivered to the upper third of the nasal cavity where the cells bypass the blood-brain barrier and enter the brain to carry out the missing metabolic function. More generally, genetically-engineered therapeutic cells of the present invention may act as mini biological factories that produce and release one or more of the following: an enzyme, a growth factor, an anti-inflammatory agent, a neurotransmitter, a neuromodulator, an anti-oxidant, etc. that can benefit the subject in need thereof. Alternatively, therapeutic genetically-engineered cells of the present invention may comprise genetically-engineered gonadotropin-releasing hormone secreting cells to increase fertility in subjects in need thereof.

Delivery-Enhancement Agents

Certain compounds, i.e., delivery-enhancement agents, may be utilized by the present invention to assist the therapeutic cells in delivery to the central nervous system and the damaged regions therein. A preferred delivery-enhancement agent comprises hyaluronidase which has been observed to very significantly increase delivery of therapeutic cells to the CNS when applied to the upper third of the nasal cavity as either a pretreatment administered in an effective amount prior to the therapeutic cell application of the present invention, or as a component of the pharmaceutical composition comprising therapeutic cells of the present invention, or as a separate compound administered intranasally to the upper third of the nasal cavity substantially simultaneously as the therapeutic cells and/or pharmaceutical composition. It is believed that the hyaluronidase acts on hyaluronic acid in the extracellular matrix to enhance delivery of therapeutic cells and/or pharmaceutical compositions comprising therapeutic cells to the CNS. Example 2 infra illustrates the increase of effectiveness by such a delivery-enhancement agent on the delivery of therapeutic cells to the CNS.

Alternative delivery-enhancement agents comprise neuregulin, migration-inducing activity and leukemia inhibitory factor. These delivery-enhancement agents, e.g., hyaluronidase, lipophilic agents, neuregulin, migration-inducing activity and leukemia inhibitory factor may be used individually, or in any combination, to enhance delivery of the therapeutic cells to the CNS according to the present invention. Therefore, at least one delivery-enhancement agent may be used as a pretreatment to transportation of the therapeutic cells and/or pharmaceutical composition and/or as a component of the pharmaceutical composition comprising therapeutic cells.

Alternative delivery-enhancement agents that further enhance the mucosal delivery of therapeutic cells and/or pharmaceutical composition comprising therapeutic cells of the present invention, comprise an enzyme inhibitor, particularly proteases inhibitors as is well known to those in the art. Protease inhibitors may include, but are limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH2, DAPT, diprotin A and B, ebelactone A and B, foroxymithine, leupeptin, pepstatin A, phosphoramidon, aprotinin, puromycin, BBI, soybean trypsin inhibitor, phenylmethylsulfonyl fluoride, E-64, chymostatin, 1,10-phenanthroline, EDTA and EGTA.

Still further alternative delivery-enhancement agents may include, but are not limited to, surfactants, bile salts, dihydrofusidates, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof; mucolytic agents, enzymes specifically targeted to a selected membrane component, inhibitors of fatty acid synthesis and inhibitors of cholesterol synthesis. The present invention contemplates using one or more, i.e., at least one, of the above delivery-enhancement agents, either alone or in combination with the therapeutic cells as a pharmaceutical compound in an effective amount.

Regulatory Agents

Certain regulatory agents to regulate, inter alia, growth and differentiation of the delivered therapeutic cells within the CNS are within the scope of the present invention and include, for example, an effective amount of regulatory agents that promote the survival of the donor cells by modulating the immune and inflammatory response. Such regulatory agents include, for example, cyclosporin and various other immunomodulators, including, interleukins (i.e., IL-1, IL-2, IL-3, IL-4, IL-5, IL-6, IL-7, IL-8, IL-9, IL-10); tumor necrosis factors (i.e., TNF-alpha and TNF-beta); and, interferons (i.e., IFN-alpha, IFN-beta, IFN-gamma, IFN-omega, and IFN-tau); and any biologically active variants thereof. Further details regarding the administration of these immunomodulating agents by the methods of the present invention can be found in U.S. patent Ser. No. 09/733,168, entitled "Methods for Administering a Cytokine to the Central Nervous System and the Lymphatic System," filed on Dec. 9, 2000, herein incorporated by reference.

Additional regulatory agents that find use in the methods of the invention include CAP23, a major cortical cytoskeleton-associated and calmodulin binding protein, and GAP43, a neural growth-associated protein. See, for example, Frey et al. (2000) J. Cell. Biol. 7:1443-1453. Further agents of interest include Osteogenic Protein-1 (OP-1) which is a morphogenic protein that stimulates growth, differention, and differentiation maintenance (U.S. Pat. No. 6,153,583); sonic hedgehog, a polypeptide shown to promote the survival of dopaminergic neurons (Miao et al. (1996) Cell Transplant 55:2-17); various other glial growth factors (U.S. Pat. Nos. 5,716,930; 6,147,190; and 5,530, 109); and any biologically active variants thereof. All of these references are herein incorporated by reference.

Other regulatory agents of interest and within the scope of the present invention comprise growth factors. As used herein "growth factor" refers to a polypeptide capable of regulating the development of the transplanted donor cell. Growth factors useful in the methods of the present invention include, but are not limited to, members of the neurotrophin family (i.e., nerve growth factor (NGF), brain-derived neurotrophic factor (BDNF), neurotrophin-3 (NT-3), and neurotrophin-4 (NT-4, also known as NT-4/5 or NT-5); fibroblast growth factors (FGFs, i.e., basic fibroblast growth factor); epidermal growth factor family (i.e., EGF, TGF.alpha., amphiregulin, heparin-binding EGF-like growth factor (HB-EGF), batacelluin (BTC), and the neuregulin group); platelet-derived growth factor; insulin; insulin-like growth factors (i.e., IGF-I and IGF-2); ciliary neurotrophic factor (CNTF), glia cell line-derived neurotrophic factor family (GDNF) (i.e., GDNF and neurturin (NTN), persephin (PSP), and artemin (ART)); transforming growth factor .beta. superfamily (i.e., subfamilies include TGF beta 1, TGF beta 2, TGF beta 3, TGF beta 4, TGF beta 5, activin, inhibin, decapentaplegic); growth differentiation factors (GDF) (i.e., GDF1, GDF2, GDF3, GDF5, GDF6, GDF7, GDF8, GDF9, GDF9B, GDF10, GDF11, and GDF15); glia-derived nexin; activity dependent neurotrophic factor (ADNF); glial growth factor (GGF); and the like. It is further recognized that any biologically active variant of these growth factors is also useful in the methods of the present invention.

The regulatory agent of present invention may be from any animal species including, but not limited to, rodent, avian, canine, bovine, porcine, equine, and, preferably, human. Preferably the regulatory agent administered is from the same species as the animal undergoing treatment.

Biologically active variants of regulatory polypeptides (i.e., growth factors, such as IGF-I, NGF, and basic FGF, cytokines, etc.) are also encompassed by the various methods and pharmaceutical compositions of the present invention. Such variants should retain the biological activity of the regulatory agent, particularly the ability to regulate the development of the donor cell (i.e., promote the survival, maintain the desired phenotype, and/or regulate the developmental cues produced by the donor cell). For example, when the regulatory polypeptide is a growth factor, such as IGF-I, NGF-I, or a member of the FGF family, the ability to bind their respective receptor sites will be retained. Such receptor binding activity may be measured using standard bioassays.

One such regulatory agent, a growth factor, that is useful in the present invention is IGF-I. The term "IGF-I" as used herein refers to insulin-like growth factor I (IGF-I), a single-chain peptide having 70 amino acids and a molecular weight of about 7,600 daltons. Insulin-like growth factor I stimulates mitosis and growth processes associated with cell development. The amino acid and nucleotide sequence for IGF-I is known in the art. See, for example, U.S. Pat. No. 5,324,639 which discloses the human IGF-I sequence; Genbank Accession No. X15726, which discloses the sequence of bovine IGF-I; and Genbank Accession No. X06043 which discloses the sequence of rat IGF-I. Each of these references is herein incorporated by reference.

In another embodiment of the present invention, the regulatory agent may comprise a member of the FGF family of growth factors and/or biologically active variants thereof. The fibroblast growth factor family encompasses a group of structurally related proteins that bind heparin with a high affinity. FGF family members have mitogen activity and induce the proliferation of a wide variety of cell types. FGF family members also participate in angiogenesis, differentiation, cell migration, embryo development, and neuronal maintenance/survival. The term "FGF" as used herein refers to a member of the fibroblast growth factor family including, for example, FGF-1 (acidic FGF), FGF-2 (basic FGF), FGF-3, FGF-4, FGF-5, FGF-6, FGF-8, FGF-9, FGF-98, or a biologically active fragment or variant thereof. The amino acid sequence and methods for making many of the FGF family members are well known in the art.

In another embodiment of the present invention, the regulatory agent may be nerve growth factor (NGF) or a biologically active variant thereof. NGF was originally isolated as a complex having a molecular weight of 130 kDa and a sedimentation coefficient of 7S. This 7S complex included three types of subunits, with the ".beta." subunit carrying all of the biological activities of NGF. Nerve growth factor stimulates mitosis and growth processes of cells, particularly nerve cells, and regulates development (i.e., influences repair, survival, and differentiation). The preferred amino acid sequence for human pre-pro-NGF and human mature NGF are provided in U.S. Pat. No. 5,288,622, which is incorporated herein by reference.

The NGF used in the present invention may be in its substantially purified, native, recombinantly produced form or in a chemically synthesized form. For example, the NGF can be isolated directly from cells naturally expressing NGF. NGF may also be recombinantly produced in eukaryotic or prokaryotic cell expression systems as described in Edwards et al, (1988) Mol. Cell. Biol. 8:2456; U.S. Pat. No. 5,986,070; and U.S. Pat. No. 6,005,081; all of which are herein incorporated by reference. Alternatively, the regulatory agent of the present invention may comprise erythropoietin (EPO), brain-derived neurotrophic factor (BDNF) and epidermal growth factor (EGF). Each of the regulatory agents described herein play a crucial role in the in-vivo survival and differentiation of the therapeutic cells of the present inventive methods and pharmaceutical compositions.

Administration of an effective amount of at least one regulatory agent by the methods of the present invention, i.e., intranasally to the upper third of the nasal cavity, alone and/or in combination with the therapeutic cells, will regulate development of the therapeutic cell transported to the CNS. The phrase "regulate development" is intended herein to mean, inter alia, that the regulatory agent potentiates the survival, differentiation, axonal development, dendritic development, and/or proliferation of the transported therapeutic cell; improves adhesion of the transported therapeutic cells to surrounding tissues (i.e., incorporation into parenchymal tissue); improves the capacity of the transported therapeutic cells to establish synaptic connection with the host neurons (Le, enhances nerve fiber formation in the donor cells; increases nerve fiber projection distances of the donor cells; or enhances nerve fiber destiny of the donor cells); and/or instructs the transported therapeutic cell to commit to a specific neural lineage (i.e., adopt a neuronal (GABA-ergic neurons, dopaminergic neurons, cholinergic neurons, hippocampal neurons, and the like), astrocytic or oligodendritic cell fate). It is further recognized that a regulatory agent can potentiate the survival of a transplanted donor cell by modulating the immune response of the subject. By "modulate" is intended the down regulation of the immune or inflammatory response (i.e., influencing systemic immune function, antigen presentation, cytokine production, lymphocyte proliferation, and entry of lymphocytes and macrophages into the CNS).

Furthermore, administration of the regulatory agent is known to "regulate development" of the invasively transplanted donor cell by influencing the developmental cues released by the transplanted donor cells (i.e., promote the donor cell to release neurotransmitters such as, dopamine, acetylcholine, GABA, or other neuroprotective factors). As such, the function and repair (i.e., enhanced nerve fiber formation, nerve fiber projection distances, and/or nerve fiber density) of the surrounding host tissue can be enhanced by the noninvasive methods of the present invention.

Delivery of an effective amount of one or more, i.e., at least one, regulatory agent to the CNS of a mammal may be achieved via administration of a pharmaceutical composition comprising a therapeutically effective dose of this agent. Alternatively, an effective amount of the at least one regulatory agent may be delivered intranasally to the upper third of the nasal cavity and/or systemically as a pretreatment, co-treatment and/or post-treatment to application of the pharmaceutical composition and/or therapeutic cell(s) of the present invention. By "effective amount" is meant, inter alia, the concentration of regulatory agent that is sufficient to elicit the desired therapeutic effect with respect to regulating the development of a donor cell, as described herein. Accordingly, an effective amount of the regulatory agent augments the clinical outcome of the cell replacement therapy in comparison to animals treated with only the cell replacement strategy. As such, a therapeutically effective dose can be assayed via a reduction in neural deficits associated with the CNS disorder being treated, and hence is characterized by an improvement in clinical symptoms.

Methods to quantify the extent of neurologic damage and to determine if the CNS disorder has been treated are well known to those skilled in the art. Such methods include, but are not limited to, histological methods, molecular marker assays, and functional/behavior analysis. For example, enhanced functional integration of the donor cells and/or enhanced function and repair of the surrounding neuronal tissue can be assayed by examining the restoration of various functions including cognitive, sensory, motor, and endocrine. Motor tests include those that quantitate rotational movement away from the degenerative side of the brain, and those that assay for balance, coordination, slowness of movement, rigidity, and tremors. Cognitive tests include memory tests and spatial learning. The specific assays used to determine treatment of a neurologic disease will vary depending on the disorder.

Desired biological activities beneficial to the regulation of transported therapeutic cell development include, for example, potentiation of the survival and/or proliferation of the transported therapeutic cells; improvement in the capacity of the transported therapeutic cell to establish synaptic connection with the host neurons; and/or instruction of the transported therapeutic cell to commit to a specific neural lineage. Methods to assay such events are known in the art. For example, an improvement in the survival of the transported therapeutic cells following the administration of the regulatory agent can be assayed using various non-invasive scans such as computerized axial tomography (CAT scan or CT scan), nuclear magnetic resonance or magnet resonance imaging (NMR or MRS) or positron emission tomography (PET) scans. Alternatively, transported therapeutic cell survival can be assayed post-mortem by microscopic examination of the region of transported therapeutic cell transplantation. The region of transported therapeutic cells can be identified, for example, by assaying for molecular markers specific to the transported therapeutic cells or alternatively, by prior incorporation of tracer dyes. Such dyes include, for example, rhodamine- or flourescein-labeled microspheres, fast blue, or retrovirally introduced histochemical markers.

The effective amount will depend on many factors including, for example, the CNS disorder being treated, the type of donor cell transplanted into the mammal, and the responsiveness of the subject undergoing treatment. It is further recognized that the therapeutically effective amount will depend on the type of developmental regulation of the transported therapeutic cell that is desired (i.e., potentiation of the survival and/or proliferation of the transported therapeutic cell; improvement of the capacity of the transported therapeutic cell to establish synaptic connection with the host neurons; regulation of the developmental cues released by the transported therapeutic cells; or improved function and repair of the surrounding neural tissue). Methods to determine efficacy and dosage are known to those skilled in the art.

For example, in Parkinson's disease, the neurons that degenerate are the dopaminergic neurons of the substantia nigra. Cell replacement strategies for patients with advanced Parkinson's disease are known and include, for example, intrastriatal grafts of nigral dopaminergic neurons from 6- to 9-week-old human embryos (Olanow at al. (1996) Trends Neurosci. 19:102-109 and Lindvall et al. (1999) Mov. Disord. 14:201-205). Delivery of pharmacologically active regulatory agents to regions of the brain affected by Parkinson's disease (i.e., midbrain and substantia nigra) is known in the art, however not in combination with intranasal delivery of therapeutic cells in such a way that the blood-brain barrier is bypassed.

As used herein, an "effective amount" of a regulatory agent in combination with transported therapeutic cells and/or pharmaceutical compositions comprising therapeutic cells of the present invention for the treatment of Parkinson's disease using the administration method of the present invention will be sufficient to reduce or lessen the clinical symptoms of Parkinson's disease. As such, an effective amount of the regulatory agent (i.e., growth factor) administered by the methods of the present invention will augment the cell replacement strategies performed under the present invention for the treatment of Parkinson's disease. Accordingly, the methods of the invention enhance survival and/or improve clinical status of the treated animals in comparison to animals treated with cell replacement strategy alone. Improvement in clinical status for Parkinson's disease includes, for example, improvement in the ventral mesencephalic graft efficacy in terms of apomorphine-induced rotational decrease, an increase in the density of striatal reinnervation, and an enhancement in neuronal survival (Tomqvist et al. (2000) Exp. Neurol. 164:130-138).

Huntington disease is characterized by progressive neurodegeneration, particularly in the striatum and cortex, which induces severe impairments in both motor and cognitive functions. Current cell replacement therapies replace inhibitor connections from the striatum to other structures such as the globus pallidus through the implantation of striatal precursor cells. Delivery of pharmacologically active regulatory agents to regions of the brain that are affected by Huntington disease (i.e., caudate-putamen, thalamus, dincephalon, cerebellum, and frontal cortex) is known in the art, though never in connection with therapeutic cells and/or pharmaceutical compositions comprising therapeutic cells of the present invention, wherein the blood-brain barrier is bypassed.

As used herein, an "effective amount" of a regulatory agent for the treatment of Huntington disease using the administration method of the present invention will be sufficient to reduce or lessen the clinical symptoms of Huntington disease. Thus, an effective amount of the regulatory agent (i.e., growth factor) administered by the methods of the present invention will augment the cell replacement strategies commonly performed under the present invention for the treatment of Huntington disease. As such, the methods of the invention enhance survival and/or improve clinical status of the treated animals in comparison to animals treated with cell replacement strategy alone. Improvement in clinical status includes, for example, disinhibition of pallidal output, reduced locomotor hyperactivity, recovery of complex motor and cognitive behavior, and restitution of new habit-learning systems in the lesioned striatum. See, for example, Bjorklund et al. (1994) Functional Neural Transplantation (Raven, N.Y.), pp. 157-195; Dunnett et al. (1995) Behav. Brain Res. 66:133-142; Kendall et al. (1998) Nat. Med. 4:727-729; Palfi et al. (1998) Nat. Med. 4:963-966; Brasted et al. (1999) Proc. Natl. Acad. Sci. USA 96:10524-10529; and Wictorin et al. (1992) Prog. Neurobiol. 38:611-639; all of which are herein incorporated by reference. Administration of regulatory agents by the methods of the present invention will be sufficient to improve the clinical outcome of the cell replacement therapy. Such assays can be readily used by one skilled in the art to determine the dosage range and/or appropriate regulatory agent of choice for the effective treatment of Huntington disease.

Ischemic damage to the CNS (and resulting cell loss and death) can result from, for example, cardiac arrest or coronary artery occlusion, or cerebral artery occlusion or stroke. Neural circuits of the CNS damaged following an ischemic event have been reconstructed using various cell replacement strategies. For instance, for focal ischemia events, implantation of embryonic striatum into the damaged striatum (Hodges et al. (1994) Functional Neural Transplantation (Raven, N.Y.), pp. 347-386) and implantation of neurons derived from a human teratocarcinoma cell line (Borlongan et al. (1998) Exp. Neurol. 149:310-321 and Borlongan et al. (1998) Neuroreport 9:3703-3709) have been performed. See also, for example, Hodges et al. (1996) Neurosci. 72:959-988, Sorensen et al. (1996) Exp. Neurol. 138:227-235, and Sinden et al. (1997) Neurosci. 81:599-608.

As used herein, an "effective amount" of a regulatory agent for the treatment of ischemic injury will be sufficient to reduce or lessen the clinical symptoms of the ischemic event. As such, an effective amount of the regulatory agent administered by the methods of the present invention will augment the cell replacement strategies commonly performed according to the present invention for the treatment of an ischemic injury. Improvement in clinical status includes, for example, a reduction in infarct size, edema, and/or neurologic deficits (Le., improved recovery of motor, sensory, vestibulomotor, and/or somatosensory function). Improvements further encompass a reduction in neural deficits, and hence improved recovery of motor, sensory, vestibulomotor, and/or somatosensory function.

Methods to determine if an ischemic event has been treated, particularly with regard to reduction of ischemic damage including infarct size, edema, and development of neural deficits, are well known to those skilled in the art. For example, after ischemic injury, there is a significant increase in the density of omega 3 (peripheral-type benzodiazepine) binding sites (Benazodes et al. (1990) Brain Res. 522:275-289). Methods to detect omega 3 sites are known and can be used to determine the extent of ischemic damage. See for example, Gotti et al. (1990) Brain Res. 522:290-307 and references cited therein. Alternatively, Growth Associated Protein-43 (GAP-43) can be used as a marker for new axonal growth following an ischemic event. See, for example, Stroemer et al. (1995) Stroke 26:2135-2144, and Vaudano et al. (1995) J. Neurosci 15:3594-3611. The therapeutic effect may also be measured by improved motor skills, cognitive function, sensory perception, speech and/or a decrease in the propensity to seizure in the mammal undergoing treatment. Such functional/behavior tests used to assess sensorimotor and reflex function are described in, for example, Bederson et al. (1986) Stroke 17:472-476, DeRyck et al. (1992) Brain Res. 573:44-60, Markgraf et al. (1992) Brain Res. 575:238-246, Alexis et al. (1995) Stroke 26:2338-2346. Enhancement of neuronal survival may also be measured using the Scandinavian Stroke Scale (SSS) or the Barthel Index. Such assays can be readily used by one skilled in the art to determine the dosage range and/or appropriate regulatory agent of choice for the effective treatment of an ischemic event.

For purposes of regulating the development of a therapeutic cell(s) of the present invention following intranasal transportation into the CNS with bypass of the blood-brain barrier in a mammal, the therapeutically effective amount or dose of a regulatory agent may comprise about 0.002 mg/kg to about 2.0 mg/kg of body weight or from about 0.03 mg/kg to about 0.6 mg/kg of body weight. Alternatively, the regulatory agent may be administered at 0.0004, 0.001, 0.005, 0.007, 0.009, 0.01, 0.04, 0.06, 0.08, 0.1, 0.2, 0.4, 0.6, 0.8, 1.0, 1.2, 1.4, 1.6, 1.8, or 2.0 mg/kg of body weight. It is further recognized that a lower dose range of certain regulatory agents (i.e., ADNF) may be preferred. In these embodiments, the regulatory agent can be administered from about 0.1 ng/kg to about 20 ng/kg. Alternatively, the regulatory agent can be administered at 0.2, 0.4, 0.6, 0.8, 1, 2, 4, 8, 12, 15, 18, and 19 ng/kg of body weight.

Antibiotic Agents

In various embodiments, the present invention may further comprise an effective amount of at least one antibiotic, or alternatively at least one antibiotic(s) pretreatment administered prior to application of the pharmaceutical composition to the upper third of the nasal cavity may be used, or any combination thereof, to protect the patient undergoing therapeutic cell therapy. Further, the antibiotic(s) may be delivered as a pretreatment, co-treatment and/or post treatment systemically and/or by application to the upper third of the nasal cavity. The utility of such an antibiotic element within the present invention is to reduce the risk that bacteria found in the nasal cavity may enter the nasal tissues at the upper third of the nasal cavity during application of the therapeutic cell(s) and/or pharmaceutical composition, cross the blood-brain barrier and infect other tissues within the CNS. Particular tissues of concern include, but are not limited to, the brain, meninges, blood, spinal cord, and other peripheral tissues. A preferred embodiment is to pretreat and/or simultaneously treat the patient with antibiotic(s) when the delivery-enhancement agent(s), e.g., hyaluronidase, is applied to the upper third of the nasal cavity.

Exemplary antibiotics for use in the present invention comprise mupirocin, defensin, gentamycin, geneticin, cefminoxime, penicillin, streptomycin, xylitol, or other antibiotic, either alone or in combination to assist in protecting the patient who is receiving therapeutic cell(s) and/or pharmaceutical composition of the present invention. The use of such antibiotics within nasal treatments is widely reported in the literature as will be readily recognized by the skilled artisan, however no such nasal treatment is reported in conjunction with the intranasal application of therapeutic cells and/or pharmaceutical compositions comprising therapeutic cells to the upper third of the nasal cavity whereby the blood-brain barrier is bypassed.

Immunosuppressive Agents

Alternate embodiments of the present invention may further comprise an effective amount of at least one immunosuppressive agent to enhance the viability of the therapeutic cell(s) through protection from inflammatory response and/or activation of host immunocompetent cells. The immunosuppressive agent(s) may be delivered either as a pretreatment, simultaneously with the therapeutic cell(s) and/or pharmaceutical composition and/or post-treatment of the therapeutic cell(s) and/or pharmaceutical composition. Such immunosuppressive therapy in combination with the therapeutic cell(s) and/or pharmaceutical composition applied to the upper third of the nasal cavity will improve the survival of such cells.

When the host immunocompetent cells of the CNS, nasal mucosa and the neural pathway between the nasal mucosa and the CNS detect the applied therapeutic cells of the present invention, inflammatory response and/or activation of host immunocompetent cells may result. This series of events will decrease the therapeutic cell(s) survival. Therefore, immunosuppression agent(s) may be employed, prior to, during and/or after the application of therapeutic cell(s) to the upper third of the nasal cavity to play a crucial role in the survival and viability of the therapeutic cells, The immunosuppression agent(s) may be applied intranasally to the upper third of the nasal cavity and/or systemically. Conventional and well known immunosuppressive agents that may be used alone, or in combination, in the present invention comprise cyclosporine A, tacrolimus, prednisolone, azathioprine, methylprednisolone, mycophenylate mophetil and sirolimus. Another immunosuppressive agent comprises application of genetically engineered cells expressing the Fas ligand.

Pharmaceutical Composition

In addition to the effective amount of at least one therapeutic cell administered to the upper third of the mammalian nasal cavity, a pharmaceutical composition may be applied or administered to the upper third of the nasal cavity. Such a pharmaceutical composition may comprise, in addition to the effective amount of at least one therapeutic cell, for example, the composition can comprise at least one regulatory agent as described supra, at least one delivery-enhancement agent as described supra, at least one antibiotic, and/or at least one immunosuppressive agent, all as described supra and as will be discussed further infra. The pharmaceutical composition of the present invention may be combined with pre-, co-, and post-treatment with any combination of systemic and/or application to the upper third of the nasal cavity of the at least one regulatory agent, delivery-enhancement agent, antibiotic and/or immunosuppressive agent.

Among the alternatives that may be combined with therapeutic cells in the pharmaceutical composition are delivery-enhancement agents, such as lipophilic agents, that can enhance absorption of the regulatory agent through the mucosa or epithelium of the nasal cavity to reach damaged and/or degenerating cells in the CNS. The regulatory agent may be mixed with a lipophilic agent or adjuvant alone or in combination with a carrier, or may be combined with one or several types of micelle or liposome substances. Among the preferred lipophilic substances are cationic liposomes including one or more of phosphatidyl choline, lipofectin, DOTAP, or the like.

A preferred delivery-enhancement agent comprises hyaluronidase which has been observed to very significantly increase delivery of therapeutic cells to the CNS when applied to the upper third of the nasal cavity as either a pretreatment to the therapeutic cell application of the present invention, or as a component of the pharmaceutical composition comprising therapeutic cells of the present invention. Alternative delivery-enhancement agents comprise neuregulin and migration-inducing activity. These delivery-enhancement agents, e.g., hyaluronidase, lipophilic agents, neuregulin and migration-inducing activity may be used individually, or in any combination, to enhance delivery of the therapeutic cells to the CNS according to the present invention. Therefore, at least one delivery-enhancement agent may be used as a pretreatment to transportation of the therapeutic cells and/or pharmaceutical composition and/or as a component of the pharmaceutical composition comprising therapeutic cells.

The pharmaceutical composition of the present invention may further comprise at least one antibiotic, or alternatively an antibiotic pretreatment prior to application of the pharmaceutical composition to the upper third of the nasal cavity may be used, or any combination thereof, to protect the patient undergoing therapeutic cell therapy. Further, the antibiotic may be delivered as a pretreatment, co-treatment and/or post treatment given intranasally and/or systemically. The utility of such an antibiotic element within the present invention is to reduce the risk that bacteria found in the nasal cavity may enter the nasal tissues at the upper third of the nasal cavity during application of the therapeutic cell(s) and/or pharmaceutical composition, cross the blood-brain barrier and infect other tissues within the CNS. Particular tissues of concern include, but are not limited to, the brain, meninges, blood, spinal cord, and other peripheral tissues. A preferred embodiment is to pretreat and/or simultaneously treat the patient with antibiotic when a delivery-enhancement agent such as hyaluronidase is applied, either alone or in a pharmaceutical composition, to the upper third of the nasal cavity.

Exemplary antibiotics for use in the present invention comprise mupirocin, defensin, gentamycin, geneticin, cefminoxime, penicillin, streptomycin, xylitol, or other antibiotic, either alone or in combination to assist in protecting the patient who is receiving therapeutic cell(s) and/or pharmaceutical composition of the present invention. The use of such antibiotics within nasal treatments is widely reported in the literature as will be readily recognized by the skilled artisan.

The present invention may further comprise at least one immunosuppressive agent, delivered either as a pretreatment, simultaneously with the therapeutic cell(s) and/or pharmaceutical composition and/or post-treatment of the therapeutic cell(s) and/or pharmaceutical composition. Such immunosuppressive therapy in combination with the therapeutic cell(s) and/or pharmaceutical composition applied to the upper third of the nasal cavity will improve the survival of such cells. When the host immunocompetent cells of the CNS, nasal mucosa and the neural pathway between the nasal mucosa and the CNS detect the applied therapeutic cells of the present invention, inflammatory response and/or activation of host immunocompetent cells may result. This series of events will decrease the therapeutic cell(s) survival. Therefore, immunosuppression agent(s) may be employed, prior to, during and/or after the application of therapeutic cell(s) to the upper third of the nasal cavity to play a crucial role in the survival and viability of the therapeutic cells. The immunosuppression agent(s) may be applied intranasally to the upper third of the nasal cavity and/or systemically. Conventional and well known immunosuppressive agents that may be used alone, or in combination, in the present invention comprise cyclosporine A, tacrolimus, prednisolone, azathioprine, methylprednisolone, mycophenylate mophetil and sirolimus. Another immunosuppressive agent comprises application of genetically engineered cells expressing the Fas ligand.

Further, the pharmaceutical composition of the present invention may comprise any pharmaceutically acceptable additive, carrier, and/or adjuvant that can promote the transfer of this agent within or through a tissue innervated by the trigeminal nerve or olfactory nerve or along or through a neural pathway.

By "pharmaceutically acceptable carrier" is intended a carrier that is conventionally used in the art to facilitate the storage, administration, and/or the biological activity of therapeutic cell(s), regulatory agent(s), delivery-enhancement agent(s), antibiotic(s) and/or immunosuppressive agent within a pharmaceutical composition of the present invention. A carrier may also reduce any undesirable side effects of the components of such a pharmaceutical composition. A suitable carrier should be stable, i.e., incapable of reacting with other ingredients in the formulation. It should not produce significant local or systemic adverse effect in recipients at the dosages and concentrations employed for treatment. Such carriers are generally known in the art.

Suitable carriers for the various embodiments of the present invention include those conventionally used for large stable macromolecules such as albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like. A further pharmaceutical composition may comprise microparticles, organic and inorganic compounds serving as an adherence material for the cell(s) and cell conglomerates that may be transported to the CNS in various embodiments of the present invention, thus diminishing the loss of cells transported from the nasal mucosa to the CNS. These compounds may include several kinds of adhesive molecules, gels (serving as an encapsulating/embedding material for the cells), components of extracellular matrix or matrices, and organic and/or inorganic particles such as fibrin or fibronectin carbon- or clay- and dextran particles and their composition.

Water, saline, aqueous dextrose, and glycols are preferred liquid carriers, particularly (when isotonic) for solutions. The carrier can be selected from various oils, including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like. Where the carrier is a liquid, it is preferred that the carrier be hypotonic or isotonic with body fluids and have a pH within the range of 4.5-8.5.

Other acceptable components in the pharmaceutical composition comprise, without limitation, isotonicity-modifying agents such as water, saline, and buffers including phosphate, citrate, succinate, acetic acid, and other organic acids or their salts. Typically, the pharmaceutically acceptable carrier also includes one or more stabilizers, reducing agents, anti-oxidants and/or anti-oxidant chelating agents. The use of buffers, stabilizers, reducing agents, anti-oxidants and chelating agents in the preparation of protein-based compositions, particularly pharmaceutical compositions, is well known in the art. See, Wang et al. (1980) J. Parent. Drug Assn, 34(6):452-462; Wang et al. (1988) J. Parent. Sci. Tech. 42:S4-S26 (Supplement); Lachman et al. (1968) Drug and Cosmetic Industry 102(1):36-38, 40, and 146-148; Akers (1988) J. Parent. Sci. Tech. 36(5):222-228; and Methods in Enzymology, Vol. XXV, ed. Colowick and Kaplan, "Reduction of Disulfide Bonds in Proteins with Dithiothreitol," by Konigsberg, pp. 185-188.

Various embodiments of the pharmaceutical composition of the present invention comprise suitable buffers such as acetate, adipate, benzoate, citrate, lactate, maleate, phosphate, tartarate, borate, tri(hydroxymethyl aminomethane), succinate, glycine, histidine, the salts of various amino acids, or the like, or combinations thereof. See Wang (1980) supra at page 455. Suitable salts and isotonicifiers include sodium chloride, dextrose, mannitol, sucrose, trehalose, or the like.

Various embodiments of the pharmaceutical composition of the present invention may further comprise suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2-3); and thioglycerol at 0.1% to 0.5% (pH 3.5 to 7.0) and glutathione. Suitable antioxidants include sodium bisulfite, sodium sulfite, sodium metabisulfite, sodium thiosulfate, sodium formaldehyde sulfoxylate, and ascorbic acid. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See, e.g., Wang (1980) supra at pages 457-458 and 460-461, and Akers (1988) supra at pages 224-227.

Various embodiments of the pharmaceutical composition of the present invention may further comprise one or more preservatives such as phenol, cresol, paraaminobenzoic acid, BDSA, sorbitrate, chlorhexidine, benzalkonium chloride, or the like. Suitable stabilizers include carbohydrates such as trehalose or glycerol. The composition can include a stabilizer such as one or more of microcrystalline cellulose, magnesium stearate, mannitol, or sucrose to stabilize, for example, the physical form of the composition; and one or more of glycine, arginine, hydrolyzed collagen, or protease inhibitors to stabilize, for example, the chemical structure of the composition.

Various embodiments of the pharmaceutical composition of the present invention may also comprise suitable suspending agents such as carboxymethyl cellulose, hydroxypropyl methylcellulose, hyaluronic acid, alginate, chondroitin sulfate, dextran, maltodextrin, dextran sulfate, or the like. The composition can include an emulsifier such as polysorbate 20, polysorbate 80, pluronic, triolein, soybean oil, lecithins, squalene and squalanes, sorbitan treioleate, or the like.

The pharmaceutical composition of the present invention may further comprise at least one antimicrobial such as phenylethyl alcohol, phenol, cresol, benzalkonium chloride, phenoxyethanol, chlorhexidine, thimerosol, or the like. Suitable thickeners include natural polysaccharides such as mannans, arabinans, alginate, hyaluronic acid, dextrose, or the like; and synthetic ones like the PEG hydrogels of low molecular weight; and aforementioned suspending agents may be included in the pharmaceutical composition of the present invention.

The inventive pharmaceutical composition may further comprise include an adjuvant such as cetyl trimethyl ammonium bromide, BDSA, cholate, deoxycholate, polysorbate 20 and 80, fusidic acid, or the like. Suitable sugars include glycerol, threose, glucose, galactose, mannitol, and sorbitol.

Various embodiments of the pharmaceutical composition of the present invention may further comprise one or more of a solubility enhancing additive, preferably a cyclodextrin; a hydrophilic additive, preferably a monosaccharide or oligosaccharide; an absorption promoting additive, preferably a cholate, a deoxycholate, a fusidic acid, or a chitosan; a cationic surfactant, preferably a cetyl trimethyl ammonium bromide; a viscosity enhancing additive, preferably to promote residence time of the composition at the site of administration, preferably a carboxymethyl cellulose, a maltodextrin, an alginic acid, a hyaluronic acid, or a chondroitin sulfate; or a sustained release matrix, preferably a polyanhydride, a polyorthoester, a hydrogel, a particulate slow release depo system, preferably a polylactide co-glycolides (PLG), a depo foam, a starch microsphere, or a cellulose derived buccal system; a lipid-based carrier, preferably an emulsion, a liposome, a niosome, or a micelle. The composition can include a bilayer destabilizing additive, preferably a phosphatidyl ethanolamine; a fusogenic additive, preferably a cholesterol hemisuccinate.

The pharmaceutical composition may additionally include a solubilizing compound to enhance stability of the regulatory agent or biologically active variant thereof. For IGF-I, a preferred solubilizing agent includes a guanidinium group that is capable of enhancing its solubility. Examples of such solubilizing compounds include the amino acid arginine, as well as amino acid analogs of arginine that retain the ability to enhance solubility of IGF-I or biologically active variant thereof at pH 5.5 or greater. Such analogs include, without limitation, dipeptides and tripeptides that contain arginine. By "enhancing the solubility" is intended increasing the amount of growth factor or biologically active variant thereof that can be dissolved in solution at pH 5.5 or greater in the presence of a guanidinium-containing compound compared to the amount of this protein that can be dissolved at pH 5.5 or greater in a solution with the same components but lacking the guanidinium-containing compound. The ability of a guanidinium-containing compound to enhance the solubility of the growth factor or biologically active variant thereof can be determined using methods well known in the art. In general, it is known to provide the concentration of the solubilizing compound present in the composition in the range from about 10 mM to about 1 M, and, for example, in the case of the compound arginine, in a concentration range of about 20 mM to about 200 mM.

These lists of carriers and additives are by no means complete, and a worker skilled in the art can choose excipients from the GRAS (generally regarded as safe) list of chemicals allowed in the pharmaceutical preparations and those that are currently allowed in topical and parenteral formulations.

Moreover, the method for formulating a pharmaceutical composition is generally known in the art. A thorough discussion of formulation and selection of pharmaceutically acceptable carriers, stabilizers, and isomolytes can be found in Remington's Pharmaceutical Sciences (18.sup.th ed.; Mack Publishing Company, Eaton, Pa., 1990), herein incorporated by reference.

For the purposes of this invention, the pharmaceutical composition as described herein can be formulated in a unit dosage and in a form such as a solution, suspension, or emulsion for application to the upper third of the nasal cavity. The pharmaceutical composition to be applied and administered to the upper third of the nasal cavity to the tissue innervated by the olfactory neurons may be in the form of a powder, a granule, a solution, a spray (e.g., an aerosol), an ointment, an infusion, a drop, or a sustained-release composition, such as a polymer disk. Other forms of compositions for administration include a suspension of a particulate, such as an emulsion, a liposome, an insert that releases the pharmaceutical composition slowly, and the like. The powder or granular forms of the pharmaceutical composition may be combined with a solution and with a diluting, dispersing, or surface active regulatory agent. The composition can also be in the form of lyophilized powder, which can be converted into solution, suspension, or emulsion before administration. The pharmaceutical composition comprising at least one regulatory agent is preferably sterilized by membrane filtration and is stored in unit-dose or multi-dose containers such as sealed vials or ampoules.

Administration of Therapeutic Cells and/or Pharmaceutical Compounds

Administering therapeutic cells according to the methods of the invention may include application of therapeutic cells alone or formulating the therapeutic cells with one or more of the compounds described supra as pharmaceutical compositions and administering the pharmaceutical compositions to an animal subject or host, including a human patient, intranasally to the upper third of the nasal cavity. The therapeutic cells and/other components of the pharmaceutical composition thereof, e.g., delivery-enhancement agent, regulatory agent, antibiotic and/or immunosuppressive agent, may be administered at one of a variety of doses sufficient to provide an effective amount at the desired point of action of the therapeutic cell and/or pharmaceutical composition component. Doses for humans and other mammals can range from about 0.001 mg/kg to about 100 mg/kg, preferably from about 0.01 mg/kg to about 10 mg/kg, preferably from about 0.1 mg/kg to about 1-10 mg/kg. As noted, delivery-enhancement agent(s), regulatory agent(s), antibiotic(s) and/or immunosuppressive agent(s) may be delivered as pre-treatment, co-treatment and/or post-treatment with the therapeutic cell(s) and/or pharmaceutical composition, either alone or as a component of the pharmaceutical composition, and, when not comprised within the pharmaceutical composition, may be delivered either systemically or to the upper third of the nasal cavity.

For application to the upper third of the nasal cavity as suspensions, aerosols, sprays or drops, the therapeutic cell(s) and/or pharmaceutical composition(s) can be prepared according to techniques well known in the art of pharmaceutical formulation. The compositions can be prepared as suspensions of cells in solutions which may comprise salts such as saline, components such as phosphate, succinate or citrate buffers to maintain pH, osmoregulatory and osmotic agents such as taurine, and suitable preservatives, absorption promoters to enhance bioavailability, fluorocarbons or other solubilizing or dispersing agents known in the art. The means of applying a pharmaceutical composition intranasally to the upper third of the nasal cavity may be in a variety of forms such as a powder, spray, gel or nose drops.

Other forms of compositions for administration of therapeutic cells and/or pharmaceutical compositions or elements thereof include a suspension of a particulate, such as an emulsion, a liposome, or in a sustained-release form to prolong the presence of the pharmaceutically active agent in an individual. The powder or granular forms of the pharmaceutical composition may be combined with a solution and with a diluting, dispersing or surface-active agent. Additional compositions for administration include a bioadhesive to retain the agent at the site of administration at the upper third of the nasal cavity, for example a spray, paint, or swab applied to the mucosa. A bioadhesive can refer to hydrophilic polymers, natural or synthetic, which, by the hydrophilic designation, can be either water soluble or swellable and which are compatible with the pharmaceutical composition. Such adhesives function for adhering the formulations to the mucosal tissues of the upper third of the nasal cavity. Such adhesives can include, but are not limited to, hydroxypropyl cellulose, hydroxypropyl methylcellulose, hydroxy ethylcellulose, ethylcellulose, carboxymethyl cellulose, dextran, guar gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and combinations thereof. The composition can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampoules.

The pharmaceutical composition may be formulated in a sustained-release form to prolong the presence of the active agent in the treated individual. Many methods of preparation of a sustained-release formulation are known in the art and are disclosed in Remington's Pharmaceutical Sciences. Generally, the therapeutic cells, pharmaceutical composition and/or components of the pharmaceutical composition, i.e., delivery-enhancement agent, regulatory agent, antibiotic and/or immunosuppressive agent, may be entrapped in semipermeable matrices of solid hydrophobic polymers. The matrices can be shaped into films or microcapsules. Matrices can include, but are not limited to, polyesters, co-polymers of L-glutamic acid and gamma ethyl-L-glutamate, polylactides, polylactate polyglycolate, hydrogels, non-degradable ethylene-vinyl acetate, degradable lactic acid-glycolic acid copolymers, hyaluronic acid gels, and alginic acid suspensions. Suitable microcapsules can also include hydroxymethylcellulose or gelatin and poly-methyl methacrylate. Microemulsions or colloidal drug delivery systems such as liposomes and albumin microspheres can also be used.

Delivery Systems

Therapeutic cells and/or a pharmaceutical composition comprising therapeutic cells and/or components of the pharmaceutical composition of the present invention may further be dispensed and applied intranasally to the upper third of the nasal cavity as a powdered or liquid nasal spray, suspension, nose drops, a gel, film or ointment, through a tube or catheter, by syringe, by packtail, by pledget (a small flat absorbent pad), by nasal tampon or by submucosal infusion. In some aspects of the present invention, the methods comprise administering to an individual therapeutic cells and/or a pharmaceutical composition thereof to the upper third of the nasal cavity by way of a delivery device. Nasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. In some aspects, an accurate effective dosage amount is contained within a bioadhesive patch that is placed directly within and on the upper third of a nasal cavity.

Therapeutic cells and/or a pharmaceutical composition comprising therapeutic cells and/or components of the therapeutic composition of the present invention may be conveniently delivered to the upper third of the nasal cavity in the form of an aerosol spray using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the therapeutic cells and/or pharmaceutical composition as will be readily recognized by the skilled artisan. In the case of a pressurized aerosol, the dosage unit may be controlled by providing a valve to deliver an accurately metered amount.

The means to deliver therapeutic cells or pharmaceutical composition comprising therapeutic cells and/or components of the pharmaceutical composition of the present invention to the upper third of the nasal cavity as a powder may be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the upper third of the nasal cavity. In this embodiment, the therapeutic cells may be dehydrated and/or lyophilized, with subsequent rehydration in the nasal mucosa.

Intermittent and Cyclic Dosing

In various embodiments of the invention, therapeutic cells and/or a pharmaceutical composition comprising an effective amount of the therapeutic cells and/or the components of the pharmaceutical composition may be administered as a single and one-time dose, or alternatively therapeutic cells and/or the components of the pharmaceutical composition may be administered more than once and intermittently. By "intermittent administration" is intended administration of an effective amount of therapeutic cells and/or the components of the pharmaceutical composition, followed by a time period of discontinuance, which is then followed by another administration of an effective amount, and so forth. Administration of the effective amount of therapeutic cells and/or the components of the pharmaceutical composition may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the therapeutic cells and/or the components of the pharmaceutical composition. The time period of discontinuance may be longer or shorter than the period of continuous sustained-release or daily administration. During the time period of discontinuance, the therapeutic cells and/or the components of the pharmaceutical composition level in the relevant tissue is substantially below the maximum level obtained during the treatment. The preferred length of the discontinuance period depends on the concentration of the effective dose and the form of therapeutic cells and/or the components of the pharmaceutical composition used. The discontinuance period can be at least 2 days, preferably is at least 4 days, more preferably is at least 1 week and generally does not exceed a period of 4 weeks. When a sustained-release formulation is used, the discontinuance period must be extended to account for the greater residence time of regulatory agent at the site of injury. Alternatively, the frequency of administration of the effective dose of the sustained-release formulation can be decreased accordingly. An intermittent schedule of administration of therapeutic cells and/or the components of the pharmaceutical composition may continue until the desired therapeutic effect, and ultimately treatment of the disease or disorder is achieved.

In yet another embodiment, intermittent administration of the effective amount(s) of therapeutic cells and/or the components of the pharmaceutical composition is cyclic. By "cyclic" is intended intermittent administration accompanied by breaks in the administration, with cycles ranging from about 1 month to about 2, 3, 4, 5, or 6 months. For example, the administration schedule might be intermittent administration of the effective dose of therapeutic cells and/or the components of the pharmaceutical composition, wherein a single short-term dose is given once per week for 4 weeks, followed by a break in intermittent administration for a period of 3 months, followed by intermittent administration by administration of a single short-term dose given once per week for 4 weeks, followed by a break in intermittent administration for a period of 3 months, and so forth. As another example, a single short-term dose may be given once per week for 2 weeks, followed by a break in intermittent administration for a period of 1 month, followed by a single short-term dose given once per week for 2 weeks, followed by a break in intermittent administration for a period of 1 month, and so forth. A cyclic intermittent schedule of administration of therapeutic cells and/or the components of the pharmaceutical composition to a subject may continue until the desired therapeutic effect, and ultimately treatment of the disorder or disease is achieved.

For purposes of regulating therapeutic cell development and thereby reducing or preventing the clinical manifestation of the neurological disorder being treated, intranasal administration of one or more therapeutically effective doses of at least one regulatory agent may occur within minutes, hours, days, or even weeks of the initial application of the therapeutic cells and/or pharmaceutical composition(s) of the present invention. For example, the initial therapeutic dose of the at least one regulatory agent may be administered within about 2 to 4 hours, within about 2 to 6 hours, within about 8 hours, within about 10 hours, about 15 hours, about 24 hours, within about 36 hours, 48 hours, 72 hours, or about 96 hours, or longer following application of the therapeutic cells and/or pharmaceutical composition(s) of the present invention. One or more additional doses of the regulatory agent may be administered for hours, days, or weeks following the initial dose. Furthermore, the animal undergoing a cell replacement regeneration therapy according to embodiments of the present invention may be administered additional regulatory agents and/or therapeutic cells and/or pharmaceutical compositions intermittently over time according to a patient care strategy. Thus, for example, an animal undergoing cell replacement therapy can be administered one or more therapeutically effective doses of the regulatory agent(s), therapeutic cells and/or pharmaceutical composition(s) of the present invention thereof prior to, during, or following the initial application. Similarly, the delivery enhancement agent, immunosuppressive agent(s) and/or antibiotic agent(s) may be administered prior to, during or following the initial application of the therapeutic cells and/or pharmaceutical composition(s) of the present invention. The intermittent and cyclic administration frameworks provided herein are exemplary only and not in any way intended to be limiting. Those skilled in the art will recognize various administration frameworks/frequencies for individual cases, each such administration framework/frequency is within the scope of the present invention.

Articles and Methods of Manufacture

The present invention also includes an article of manufacture providing therapeutic cells and/or pharmaceutical composition comprising therapeutic cells and/or components of the pharmaceutical composition of the present invention for intranasal administration to the upper third of the nasal cavity and subsequent bypass of the blood-brain barrier and transport to the CNS. The article of manufacture may include a vial or other container that contains a composition suitable for the present method together with any carrier, either dried or in liquid form. The article of manufacture further includes instructions in the form of a label on the container and/or in the form of an insert included in a box in which the container is packaged, for the carrying out the method of the invention. The instructions can also be printed on the box in which the vial is packaged. The instructions contain information such as sufficient dosage and administration information so as to allow the subject or a worker in the field to administer the therapeutic cells and/or pharmaceutical composition comprising therapeutic cells and/or components of the pharmaceutical composition of the present invention. It is anticipated that a worker in the field encompasses any doctor, nurse, technician, spouse, or other caregiver that might administer the therapeutic cells and/or pharmaceutical composition comprising therapeutic cells and/or components of the pharmaceutical composition of the present invention. The therapeutic cells and/or the components of the pharmaceutical composition may also be self-administered by the subject.

The present invention may be better understood with reference to the following examples. These examples are intended to be representative of specific embodiments of the invention, and are not intended as limiting the scope of the invention.

EXAMPLES

Example 1

Therapeutic Cells Bypassing the Blood-Brain Barrier Following Intranasal Application to the Upper Third of the Nasal Cavity in a Rat Model of Parkinson's Disease The hypothesis that therapeutic cells could indeed bypass the blood-brain barrier was tested by the inventors in healthy rodents (mice and rats) and in rats treated with 6-OHDA to create a model of Parkinson's disease. In this example, mesenchymal stem cells, i.e., eukaryotic cells, were administered intranasally to the upper third of the nasal cavity of adult healthy mice and to 6-hydroxydopamine (6-OHDA) unilateral-lesioned rats to model the damaged and/or degenerating CNS of patients with Parkinson's disease. Additionally, glioma cells were intranasally administered to the upper third of the nasal cavity of young healthy rats. Within one (1) hour of administration/application, both cell types reached the olfactory bulb, cortex, hippocampus, striatum and the cerebellum of the healthy animals. In the 6-OHDA rat model of Parkinson's disease, the cells were detected 4 hours after administration. It is likely that the cells may have reached the brain in both cases in less than one hour. After the cells crossed the cribriform plate, two migration routes were observed: (1) migration into the olfactory bulb and also to other parts of the brain including the cortex and striatum; and (2) entry into the cerebrospinal fluid with movement along the surface of the cortex followed by entrance into the brain parenchyma.

Example 2

Effect of Delivery-Enhancement Agent on Transport of Therapeutic Cells Following Intranasal Application to the Upper Third of Nasal Cavity The efficacy was evaluated of intranasal delivery of therapeutic cells to the brain after intranasal application of rat mesenchymal stem cells (MSCs) labeled with CFDA or Hoechst dye to the upper third of the nasal cavity of seven-week-old C57 bl/6 mice, thus bypassing the blood-brain barrier in the administration and application and transport of the therapeutic cells.

Initially, the animals were divided into three groups (n=5 in each group): 1) group A received only intranasal therapeutic cells; 2) group B received delivery-enhancement agent hyaluronidase intranasally 30 minutes prior to the intranasal application of cells; 3) group C received vehicle intranasally (24 µl PBS). One hour after application of cells, the animals were sacrificed under anesthesia, the skulls were frozen at −80° C. and sectioned later in sagittal or horizontal slices (20 µm) mounted with medium containing DAPI or PI and analyzed by fluorescent microscopy.

Hoechst dye labeled cells appeared in all layers of the olfactory bulb, striatum, cortex, in the wall and vicinity of the lateral ventricle, and cerebellum of animals in group A, the intranasally delivered therapeutic cells alone. In the olfactory bulb, the cells were distributed over all layers in animals of group A and B. Intranasal administration of hyaluronidase (100 U/animal in group B) increased the number of MSCs in the brain, especially in the olfactory bulb, when compared with those from group A.

The distribution of MSCs in different cortex layers in groups A and B suggest migration of therapeutic cells from the surface into the parenchyma. Numerous cells were localized in the subarachnoid space in close vicinity to MSCs which already reached the upper layer of the cortex. Some of these cells had processes suggesting progress in their differentiation. A large amount of the intranasally-applied CFDA-labeled MSCs remained in the upper nasal cavity (arrows in Figure 2D) 1 h after application indicating that therapeutic cell migration from the nasal mucosa through the cribriform plate into the brain could possibly continue for several hours and perhaps even days.

A stepwise migration of cells from the surface of the cortex into the deeper layers was observed after a certain density of cells is reached in one layer; aggregates of cells in the deeper layers appear only in the vicinity of cell rows placed closer to the surface of the cortex.

Example 3

Targeted Migration of Therapeutic Cells to Lesion within CNS Following Intranasal Application to the Upper Third of Nasal Cavity Since the results obtained and described above in Example 2 show that, besides cortex, olfactory bulb and cerebellum, intranasally applied therapeutic cells appeared also in the area of striatum, we decided to investigate, whether neurodegeneration might target the migration of applied cells to the lesion side using a model with a unilateral lesion with 6-OHDA in adult rats.

Striatal damage was induced in adult rats by unilateral injection (left hemisphere) of the neurotoxin 6-hydroxydopamine (6-OHDA) to induce a Parkinson's type model. The cells were applied in two groups of animals (n=5 in each): 1) without or 2) with intranasal hyaluronidase treatment (200 U/animal) 30 minutes prior to the intranasal administration of the cells three days after the lesion. The brains of animals were withdrawn 4 h after application of cells and frozen at −80° C. To show the degenerative changes in the left (lesioned) striatum after 6-OHDA-lesion, 10 horizontal slices from each animal were taken from the area 5 mm to 8 mm from bregma were stained for tyrosine hydroxylase (TH).

In contrast to the strong staining of nearly whole striatum with TH at the unlesioned side, the expression of TH at the lesioned side was clearly decreased. Screening of the brain slices with fluorescent microscopy revealed a notable difference in the number of cells between the lesioned and contralateral sides: the majority of CFDA labeled MSCs was found in the olfactory bulb (OB), the cortex at the level of lesion and within the lesioned striatum whereas only very few cells were found in the striatum, cortex and OB of the contralateral hemisphere. Some MSCs were occasionally found in the slices stained for TH: Interestingly very few of the MSCs which were found in OB expressed TH, whereas the majority of cells localized in the cortex in the vicinity of the lesion were TH-positive.

These results provide evidence of targeted stem cell preferential migration to the site of the lesion in 6-OHDA-lesioned rodents. Furthermore, better delivery to the brain of bone marrow stem cells was shown in the lesioned hemisphere in comparison with those in the unlesioned side using an embodiment of the present invention.

Example 4

Therapeutic Cells Comprising Tumor Cells Bypassing Blood-Brain Barrier Following Intranasal Application to the Upper Third of Nasal Cavity in Parkinson's Model This study investigates whether or not only therapeutic stem cells but also tumor cells may be delivered to the brain after intranasal administration. Intranasal administration of human Phi-Yellow and CFDA-labeled T406 glioma cells to the upper third of the nasal cavity of 10-day old rats (n=5) was achieved. One hour after administration, the animals were sacrificed. Sagittal sections (20 μm) of the whole heads of animals (including the skull and brain) were processed by fluorescent microscopy. CFDA-labeled glioma cells identified in the nasal cavity, cribriform plate, olfactory bulb, frontal cortex, and hippocampal area.

In this study, intranasal delivery of eukaryotic cells (stem cells as well as tumor cells) into the intact and lesioned brains of rodents was demonstrated. Brain tumors consist of intracranial tumors which result from abnormal or uncontrolled cell division. This can occur in the brain, the meninges, the cranial nerves or in blood vessels or lymphatics of the central nervous system. Most primary brain tumors occur in the posterior cranial fossa in children (i.e. brain stem glioma) and in the anterior portion of the cerebral hemispheres in adults. Pediatric brain tumors account for about one-fourth of pediatric cancers. There are about more than 10,000 deaths per year in the United States due to brain tumors. Most primary brain tumors originate from glial cells in the central nervous system. However, secondary brain tumors that develop from cancers elsewhere in the body and metastasize to the brain are even more common. Tumors can metastasize to the brain from the lungs, skin, kidney, breast, colon and other organs.

Brain tumors are difficult to treat because most chemotherapeutic agents do not readily cross the blood-brain barrier and it is not possible to safely and successfully remove certain types of brain tumors, e.g. brain stem gliomas, because of their location close to areas of the brain that control key autonomic functions such as breathing, heart function, etc.

Currently, researchers developing and testing new therapeutics for brain tumors need to surgically implant tumor cells into the brain of an animal to create an animal brain tumor model which can be used to test new drugs. We demonstrate here that tumor cells can be non-invasively introduced into the brain by administering them to the upper third of the nasal cavity and that hyaluronidase and other agents can be used to facilitate this process. Thus this example demonstrates that a brain tumor model can be created non-invasively without the problems associated with neurosurgery and direct implantation of tumor cells using embodiments of the present invention.

The invention has been described with reference to various specific and preferred embodiments and techniques. However, it should be understood that many variations and modifications may be made while remaining within the spirit and scope of the invention.

We claim:

1. A method for treating a damaged or degenerating or injured central nervous system of a mammal, the damage or degeneration caused by a neurological disease or condition that results in the loss or death of central nervous system cells, comprising:
    applying at least a therapeutically effective amount of therapeutic cells to the upper third of the nasal cavity of the mammal;
    enabling the therapeutic cells to access the damaged central nervous system by bypassing the blood-brain barrier; and
    thereby treating the mammal's damaged or degenerating or injured central nervous system.

2. The method of claim 1, further comprising administering the therapeutic cells to a tissue innervated by the olfactory nerve, wherein the therapeutic cells bypass the blood-brain barrier to access the damaged central nervous system; and minimizing systemic delivery of the therapeutic cells outside of the central nervous system.

3. The method of claim 2, further comprising the therapeutic cells bypassing the blood-brain barrier by migrating along a neural pathway into the damaged central nervous system.

4. The method of claim 3, further comprising the therapeutic cells preferentially migrating to an area of damage within the central nervous system.

5. The method of claim 1, wherein the therapeutic cells comprise eukaryotic cells.

6. The method of claim 1, wherein the therapeutic cells comprise stem cells.

7. The method of claim 1, wherein the therapeutic cells are capable of therapeutic action in the mammal.

8. The method of claim 1, further comprising applying the therapeutic cells to the upper third of the mammal's nasal cavity in a physiologically effective amount to provide therapeutic action comprising replacement of lost and/or dying cells in the damaged central nervous system.

9. The method of claim 1, wherein the neurological disease or condition comprises stroke.

10. The method of claim 1, wherein the neurological disease or condition comprises Huntington's disease.

11. The method of claim 1, wherein the neurological disease or condition comprises Lewy Body Dementia (LBD).

12. The method of claim 1, wherein the neurologic disease or condition comprises frontotemporal demential (FTD).

13. The method of claim 1, wherein the neurologic disease or condition comprises progressive supranuclear palsy (PSP).

14. The method of claim 1, wherein the neurologic disease or condition comprises corticobasal degeneration (CBD).

15. The method of claim 1, wherein the neurologic disease or condition comprises multiple sclerosis.

16. The method of claim 1, wherein the neurologic disease or condition comprises brain tumors.

17. The method of claim 1, wherein the neurologic disease or condition comprises spinal cord injury.

18. The method of claim 1, wherein the neurologic disease or condition comprises subarachnoid hemorrhage.

19. The method of claim 1, wherein the neurologic disease or condition comprises intracerebral hemorrhage.

20. The method of claim 1, wherein the neurologic disease or condition comprises traumatic brain injury.

* * * * *